United States Patent
Campbell et al.

(10) Patent No.: US 7,289,853 B1
(45) Date of Patent: Oct. 30, 2007

(54) HIGH FREQUENCY WIRELESS PACEMAKER

(76) Inventors: David Campbell, 1118 Continentals Way, Belmont, CA (US) 94002; Michael Lugo, 3544 Meadowlark Dr., Casper, WY (US) 82604

( * ) Notice: Subject to any disclaimer, the term of this patent is extended or adjusted under 35 U.S.C. 154(b) by 366 days.

(21) Appl. No.: 10/929,733

(22) Filed: Aug. 30, 2004

Related U.S. Application Data

(60) Provisional application No. 60/555,443, filed on Mar. 23, 2004, provisional application No. 60/498,450, filed on Aug. 28, 2003.

(51) Int. Cl.
*A61N 1/362* (2006.01)
(52) U.S. Cl. .................................................... 607/32
(58) Field of Classification Search ................ 607/32, 607/60; 128/903
See application file for complete search history.

(56) References Cited

U.S. PATENT DOCUMENTS

| | | | |
|---|---|---|---|
| 4,441,498 A * | 4/1984 | Nordling | 607/32 |
| 5,861,019 A * | 1/1999 | Sun et al. | 607/60 |
| 6,442,432 B2 * | 8/2002 | Lee | 607/59 |
| 6,577,901 B2 * | 6/2003 | Thompson | 607/60 |
| 6,763,269 B2 * | 7/2004 | Cox | 607/60 |
| 7,047,076 B1 * | 5/2006 | Li et al. | 607/36 |
| 2003/0171791 A1 * | 9/2003 | KenKnight et al. | 607/60 |
| 2004/0176811 A1 * | 9/2004 | Von Arx et al. | 607/32 |

* cited by examiner

*Primary Examiner*—Carl Layno
(74) *Attorney, Agent, or Firm*—Winthrow & Terranova, PLLC

(57) ABSTRACT

A wireless communications system optimizes performance by dividing communications functionality between a wireless pacemaker and a wireless monitoring base station according to the design constraints imposed by the system elements. Typical design constraints include high frequency operation, low pacemaker power consumption, reasonable range, high data rate, minimal RF radiation of internal circuitry, small pacemaker antenna system, simple pacemaker RF circuit design, high reliability, low pacemaker cost, and use of existing pacemaker construction methodologies.

19 Claims, 25 Drawing Sheets

HIGH FREQUENCY WIRELESS PACEMAKER

CROSS-REFERENCE TO RELATED APPLICATIONS

This application is related to U.S. provisional patent application Nos. 60/498,450 filed Aug. 28, 2003 entitled HIGH FREQUENCY PACEMAKER SOLUTION and 60/555,443 filed Mar. 23, 2004 entitled HIGH FREQUENCY PACEMAKER USING BUTTON ANTENNA, the disclosures of which are incorporated herein by reference in their entireties.

BACKGROUND OF THE INVENTION

Most pacemaker designs utilize a metallic housing to isolate a pacemaker's contents from the implanted environment in which it is installed. The material selected must be inert to the patient and must protect the electronic circuitry from bodily fluids. Titanium is a typical housing material. Electrical leads for pacemaker signals must be connected to the pacemaker using electrical feed-throughs that preserve the environmental integrity of the housing. Since the housing is made of metal and tends to exhibit the properties of a Faraday cage, RF communications designs between a pacemaker and radios outside the patient's body have traditionally used low frequency, near field solutions that can traverse the housing. Also, since a pacemaker is battery powered, available transmitter power is limited. As such, near field solutions dramatically limit range, and since these solutions are also low frequency, data rates are limited. Any RF communications systems design utilizing implantable medical devices must consider average and peak power consumption, FCC constraints (or other regulatory constraints, such as frequency of operation, bandwidth, and radiated power), antenna performance, data rate, exposure of pacemaker circuitry to RF radiation (particularly low level ECG signals), size of antenna system and associated RF circuitry, reliability, and cost (both component and manufacturing).

To maximize range and data rate, it is desirable to use a high frequency solution. The challenge is to develop a high frequency design that has acceptable antenna performance, while minimizing size, power consumption, and radiation of pacemaker circuitry. Some existing high frequency designs use an external antenna which is attached to the outside of the pacemaker housing using some type of electrical feed-throughs to connect the RF circuitry inside the pacemaker housing to the external antenna.

The present invention leverages upon several different technologies to create an antenna design and RF system that is more optimal for implanted applications.

SUMMARY OF THE INVENTION

The present invention relates generally to implanted medical devices, and more particularly to methods and apparatus for transmitting RF signals from said implanted devices or for said implanted devices to receive signals from a device located outside of the patient.

The first embodiment of the invention is a wireless communications system that optimizes performance by dividing communications functionality between a wireless pacemaker and a wireless monitoring base station according to the design constraints imposed by the system elements. Typical design constraints include high frequency operation, low pacemaker power consumption, reasonable range, high data rate, minimal RF radiation of internal circuitry, small pacemaker antenna system, simple pacemaker RF circuit design, high reliability, low pacemaker cost, and use of existing pacemaker construction methodologies.

The second embodiment of the invention is a button antenna that is constructed similarly to an electrical feed-through. The button antenna is installed in the wireless pacemaker housing using the same techniques as electrical feed-throughs. Once installed, the button antenna and the pacemaker function as a fractional wavelength ground plane antenna. The button antenna is designed to be low profile and appears as a bulge in the pacemaker housing.

The third embodiment of the invention is how the button antenna is electrically driven. Since fractional wavelength ground plane antennas have high input impedances, the power amplifier must be designed with high output voltage and high output impedance to maximize antenna output power while maximizing power added efficiency.

The fourth embodiment of the invention is based on using the wireless pacemaker housing itself as the antenna. The wireless pacemaker housing is constructed with two electrically isolated halves. These halves form the basis for a dipole antenna which is connected to internal RF circuitry.

The fifth embodiment of the invention is also based on using the wireless pacemaker housing itself as the antenna. The transmitter (or receiver) circuitry is electrically connected directly to the wireless pacemaker housing. The wireless pacemaker housing is constructed to maximize its propensity to radiate RF energy (at the frequency in question) and to minimize its effectiveness as a Faraday cage (at the frequency in question). The basic approach is to take advantage of the fact that the wireless pacemaker housing is not a perfect Faraday cage, but has a finite resistivity that can be electrically driven. Also, by making the wireless pacemaker housing electrically asymmetrical, its Faraday cage propensities can be overcome. Techniques such as selective plating with low resistivity metals can create this asymmetry. At its extreme, sections of the wireless pacemaker housing can be electrically isolated (or partitioned) to be driven as part of an antenna system. The electrical asymmetry can be achieved by making the wireless pacemaker housing physically asymmetrical.

The sixth embodiment of the invention is based upon creating an antenna by selectively plating highly conductive metals (such as silver or gold) onto the outside surface of the wireless pacemaker housing, and then making electrical connections from the circuitry inside the wireless pacemaker housing to the plated antenna.

The seventh embodiment of the invention is based on using strategically located and sized electrical apertures in the wireless pacemaker housing, which would be sealed with a hermetic material such as glass. These apertures would allow RF radiation to pass from the inside of the wireless pacemaker housing to the outside of the wireless pacemaker housing.

The eighth embodiment of the invention is used in conjunction with the sixth and seventh embodiments above and uses the wireless pacemaker housing as a passive radiator. A driven antenna would be located inside the wireless pacemaker housing, which would radiate RF energy to the wireless pacemaker housing, which would re-radiate the RF energy outside the wireless pacemaker housing.

The present invention enables design of a wireless pacemaker and wireless communications system that is optimal for its application. Namely, high frequency operation, low pacemaker power consumption, reasonable range, high data rate, minimal RF radiation of internal pacemaker circuitry, small pacemaker antenna system, simple pacemaker RF circuit design, high reliability, low pacemaker cost, and use of existing pacemaker construction methodologies. The wireless communications system may operate in the 403 MHz band intended for medical applications, the 902 to 928 MHz ISM band or any other high frequency. The wireless circuitry in the pacemaker can be designed to consume less than 10 mA (while transmitting) and communicate with a wireless monitoring base station at a distance of at least 10 feet (although significantly greater distances are possible).

Implanted medical devices are usually contained in a hermetically sealed titanium (or other metallic) housing. Normally, the only non-metallic areas of the housing are electrical "feed-throughs" which allow an electrical connection to be made from the outside of the housing to the inside of the housing and are insulated from the housing with glass (or some other sealing compound). The feed-throughs provide a means to transfer low level/low frequency electrical signals to and from the patient, such as obtaining ECG signals from the heart and sending electrical pacing signals to the heart. From a radio frequency (RF) perspective, the housing represents a Faraday cage with some holes in it. Faraday cages are traditionally used to electrically isolate the contents inside the cage from the electrical environment outside the cage, so the notion of transmitting (or receiving) an RF signal from inside the housing to a receiver (or from a transmitter) outside of the housing must overcome the shielding nature of the Faraday cage. Since most RF implementations will be using FCC Part 15 guidelines, the actual radiated RF energy is quite small; therefore, some level of inefficiency is acceptable. The present invention uses multiple approaches to create wireless pacemaker antenna systems that function effectively within the restrictions imposed by the Faraday cage.

Those skilled in the art will appreciate the scope of the present invention and realize additional aspects thereof after reading the following detailed description of the preferred embodiments in association with the accompanying drawing figures.

DETAILS OF THE INVENTION

The embodiments set forth below represent the necessary information to enable those skilled in the art to practice the invention and illustrate the best mode of practicing the invention. Upon reading the following description in light of the accompanying drawing figures, those skilled in the art will understand the concepts of the invention and will recognize applications of these concepts not particularly addressed herein. It should be understood that these concepts and applications fall within the scope of the disclosure and the accompanying claims.

Figure 1:
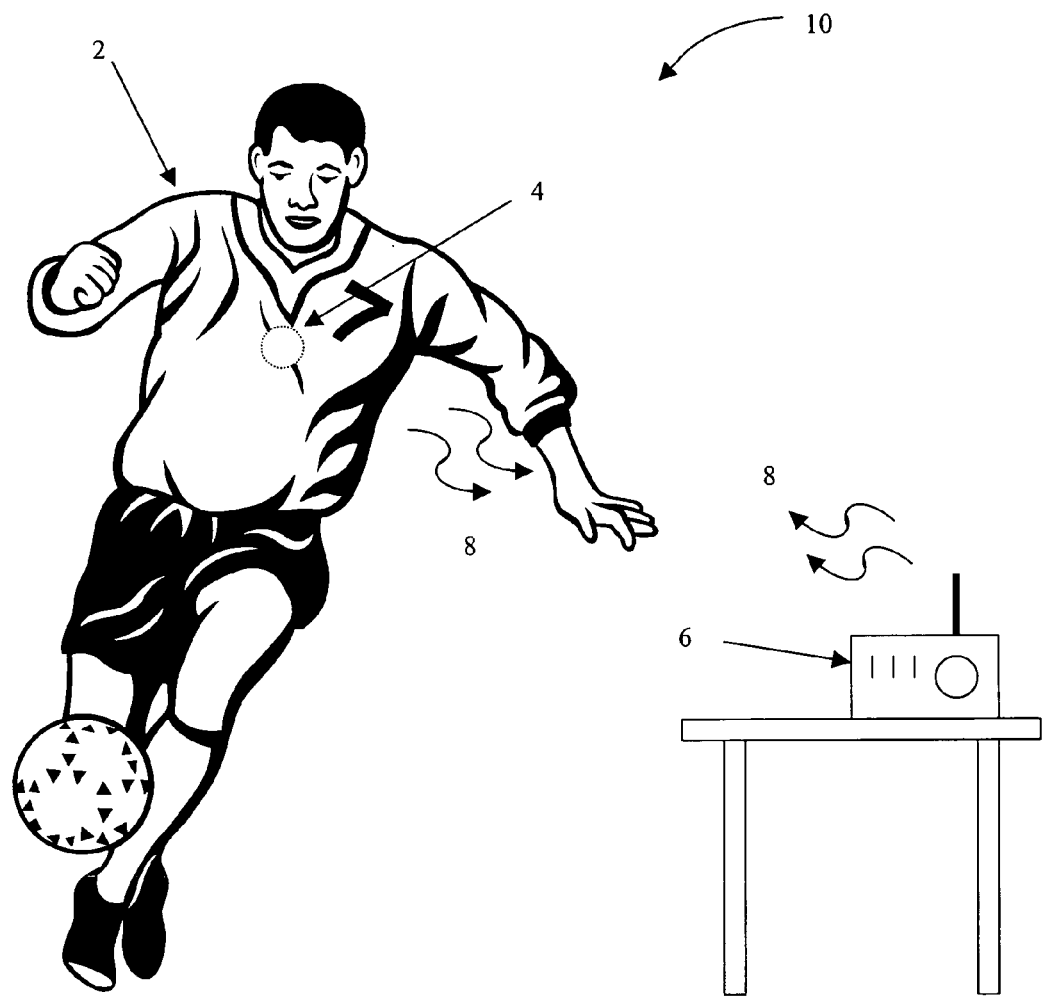
FIG. 1 shows a high frequency wireless pacemaker in a cardiac monitoring environment.

FIG. 1 shows how the invention can be used in a cardiac monitoring environment. A Patient 2 with an Implanted Wireless Pacemaker 4 is in close proximity (several feet) of a Wireless Monitoring Base Station 6. The Wireless Pacemaker 4 has been surgically implanted inside the patient's body to provide cardiac pacing and/or defibrillating and/or cardiac monitoring functions. The Wireless Pacemaker 4 and Wireless Monitoring Base Station 6 together form a Wireless Communications System 10. Under certain conditions, the Wireless Monitoring Base Station 6 will send an interrogating signal to the Wireless Pacemaker 4 to establish an exchange of information between the Wireless Pacemaker 4 and the Wireless Monitoring Base Station 6. This information is encoded onto High Frequency Radiated Radio Frequency (RF) Communications Signals 8 which are transmitted and received by the Wireless Pacemaker 4 and the Wireless Monitoring Base Station 6.

The first embodiment of the invention is comprised of an Implanted Wireless Pacemaker 4 which has been designed to provide all conventional pacemaker functionality while providing the ability to communicate with a Wireless Monitoring Base Station 6 as part of a Wireless Communications System 10. The Implanted Wireless Pacemaker 4 can be designed for two-way communications, or can be designed to only transmit to the Wireless Monitoring Base Station 6.

Figure 2:
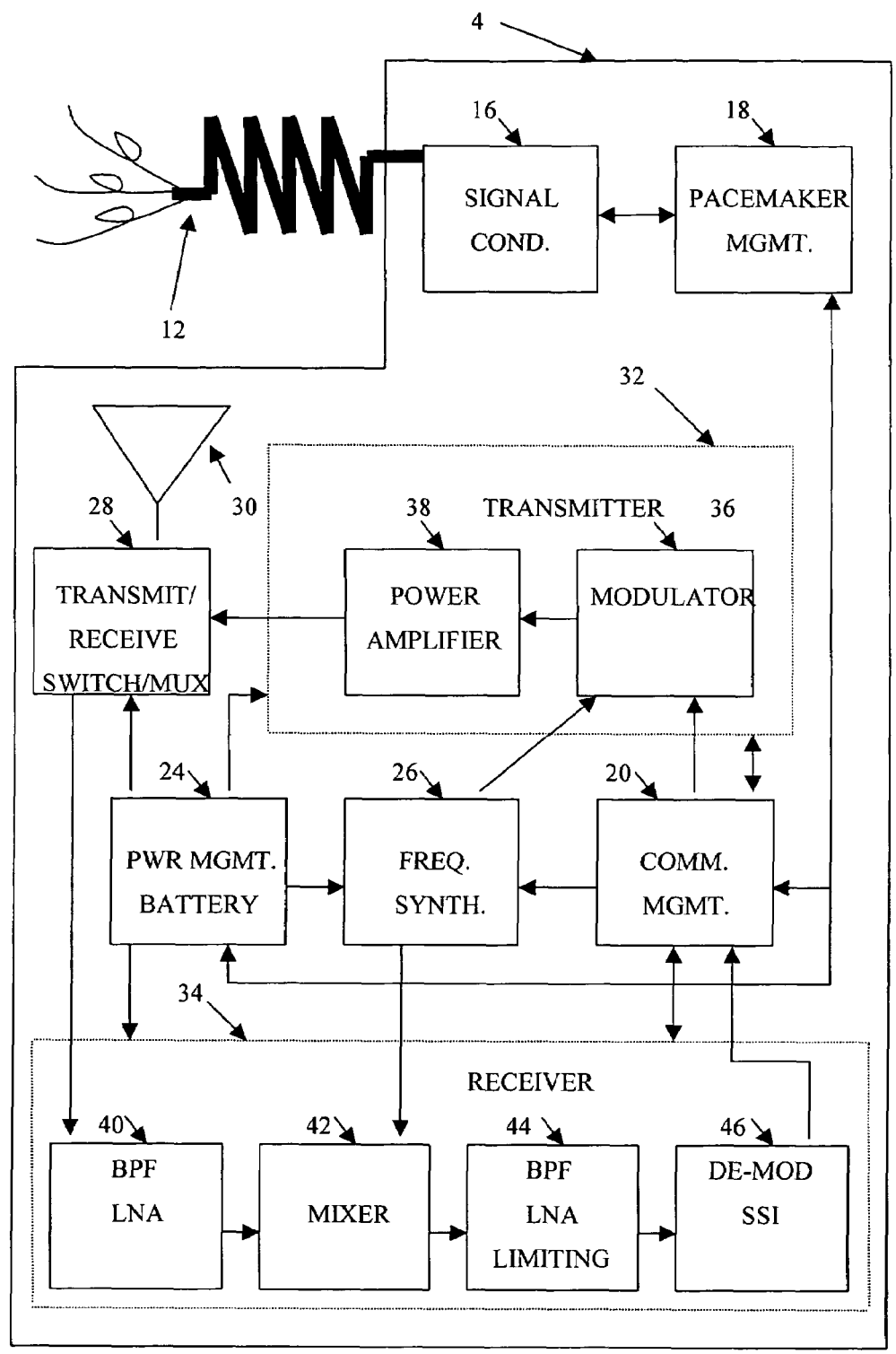
FIG. 2 shows a block diagram of an implanted wireless pacemaker with power management and control circuitry.

FIG. 2 illustrates the contents of a two-way, Implanted Wireless Pacemaker 4 which has been optimized for effective communications while minimizing battery power consumption. A set of Implanted Cardiac Leads for Monitoring and Pacing 12 is connected to Signal Conditioning Circuitry 16 in the Implanted Wireless Pacemaker 4 and provides the electrical connection to the patient for receiving electrical cardiac monitoring signals and for sending cardiac pacing signals to the patient (defibrillator signals could also be sent to the patient). Signal Conditioning Circuitry 16 conditions signals it receives and/or sends to or from the Pacemaker Processing and Control Circuitry 18 which provides the intelligence, processing, and control for the Implanted Wireless Pacemaker 4. The Pacemaker Processing and Control Circuitry 18 is connected to Communications Processing and Control Circuitry 20 and Battery and Power Management and Control Circuitry 24. This provides for management of all of the wireless circuitry in the Implanted Wireless Pacemaker 4, including transfer of transmitted and received data, and power down of any portion of the wireless circuitry when not in use to conserve battery power. A Frequency Synthesizer 26 is used to provide a precise frequency reference for both a Transmitter Modulator 36 and a Receiving Mixer 42. Use of the Frequency Synthesizer 26 provides the opportunity to receive and/or transmit on different RF channels.

A Radiating Element 30 (or antenna) provides the means for radiating and/or receiving radiated (wireless) RF signals. Several of the embodiments of the invention demonstrate ways to implement a Radiating Element 30 in an Implanted Wireless Pacemaker 4. These include several methods for using the Wireless Pacemaker Housing itself as a Radiating Element 30, methods for installing a Radiating Element 30 to or in the Wireless Pacemaker Housing, and methods for configuring a Wireless Pacemaker Housing such that a Radiating Element 30 inside the Wireless Pacemaker Housing can receive or transmit radiated RF signals from or to outside the Wireless Pacemaker Housing.

The Radiating Element 30 is connected to Transmit/Receive Switch or Multiplexor 28, which in turn provides a connection between the Radiating Element 30 and either the Transmitter Circuitry 32 or the Receiver Circuitry 34 (depending on whether the Implanted Wireless Pacemaker 4 is transmitting or receiving wireless data. The Transmitter Circuitry 32 contains a Transmitter Modulator 36 which receives data to be transmitted from the Communications Processing and Control Circuitry 20 and the RF transmit frequency from the Frequency Synthesizer 26. The Transmitter Modulator 36 drives the Transmitter Power Amplifier 38 and Impedance Matching Network (not shown) which then drives the Transmit/Receive Switch or Multiplexor 28 which is connected to the Radiating Element 30.

The Receiver Circuitry 34 contains a Receiver Impedance Matching Network, Followed by a Passive Wideband Bandpass Filter, Followed by a Wideband, High Compression Point, Low Power, Somewhat Low Sensitivity, Low Noise Amplifier 40, which feeds a Receiving Mixer 42, which receives its RF reference frequency for the selected receive channel from the Frequency Synthesizer 26. The Receiving Mixer 42 then feeds a Passive Narrowband Bandpass Filter (BPF), Followed by a Narrowband Amplifier (LNA) and Limiter 44, which then feeds a Demodulator (DEMOD) and Signal Strength Indicator (SSI) 46, which then feeds received wireless data and signal strength information to the Communications Processing and Control Circuitry 20.

In a preferred embodiment, the Implanted Wireless Pacemaker 4 would be part of a Wireless Communications System 10 using slow frequency hopping spread spectrum technology (such as the 902 MHz to 928 MHz ISM Band). All wireless communications between the Implanted Wireless Pacemaker 4 and the Wireless Monitoring Base Station 6 would be initiated by the Wireless Monitoring Base Station 6, which would send a continuous interrogation signal on a single channel long enough for the receiver circuitry in the Implanted Wireless Pacemaker 4 to scan all of the spread spectrum channels (perhaps a few milliseconds). The Wireless Monitoring Base Station 6 then waits for a reply on the same channel. If it does not receive a reply from the Implanted Wireless Pacemaker 4, then the Wireless Monitoring Base Station 6 frequency hops to the next channel and repeats the process until the Implanted Wireless Pacemaker 4 responds to the interrogating signal. The wireless circuitry in the Implanted Wireless Pacemaker 4 is in a power down state most of the time to conserve battery power. Periodically (perhaps once every second), the receiver 34 in the Implanted Wireless Pacemaker 4 is activated and quickly scans all of the spread spectrum channels looking for a channel that is being actively interrogated. When it finds an active channel, it analyzes the interrogation signal to see if this specific Implanted Wireless Pacemaker 4 is to respond. If not, or if no active channel is detected, then the wireless circuitry in the Implanted Wireless Pacemaker 4 is powered down for another power down period (perhaps once every second). Once communications is established between the Implanted Wireless Pacemaker 4 and the Wireless Monitoring Base Station 6, each transmission and reception triggers a frequency hop to the next channel.

Spread spectrum technology allows for a system that can be optimized for high frequency operation (hence high data rate), low pacemaker power consumption, reasonable range, small pacemaker antenna system, relatively simple pacemaker RF circuit design, high reliability, low pacemaker cost, and use of existing pacemaker construction methodologies.

For example, if the transmitter in the Wireless Monitoring Base Station 6 is designed to output 1 watt (+30 dbm), then the Radiating Element 30 in the Implanted Wireless Pacemaker 4 can be relatively inefficient (perhaps −20 dbi) and the Receiver Circuitry 34 in the Implanted Wireless Pacemaker 4 can be of fairly low sensitivity (perhaps −57 dbm in a system with an operating range of 10 feet with a signal margin of 10 db). A Wireless Monitoring Base Station 6-to-Implanted Wireless Pacemaker 4 link budget could look like +30 dbm (Wireless Monitoring Base Station transmitter power), +6 dbi (Wireless Monitoring Base Station antenna gain), −40 db (path loss from the Wireless Monitoring Base Station 6 to the Implanted Wireless Pacemaker 4 separated by 10 feet), −23 db (path loss through the human body to the Implanted Wireless Pacemaker 4), −20 dbi (Implanted Wireless Pacemaker antenna gain), −10 db (signal margin)=−57 dbm (Implanted Wireless Pacemaker receiver sensitivity). It is fairly straightforward to build a low cost, low power consumption, high compression point receiver with a sensitivity of −57 dbm. Such a receiver would be immune to most interfering RF signals. Also, several of the embodiments in the invention can be used to create a Radiating Element 30 with a gain of at least −20 dbi.

Now examining the opposite side of the link, if the receiver in the Wireless Monitoring Base Station 6 is designed with a receiver sensitivity of −87 dbm, then the Radiating Element 30 in the Implanted Wireless Pacemaker 4 can be relatively inefficient (perhaps −20 dbi) and the output power of the Transmitter Power Amplifier and Impedance Matching Network 38 in the Implanted Wireless Pacemaker 4 can be fairly low (perhaps +1 dbm in a system with an operating range of 10 feet with a signal margin of 10 db). An Implanted Wireless Pacemaker 4-to-Wireless Monitoring Base Station 6 link budget could look like +1 dbm (Implanted Wireless Pacemaker transmitter power), −20 dbi (Implanted Wireless Pacemaker antenna gain), −40 db (path loss from the Implanted Wireless Pacemaker 4 to the Wireless Monitoring Base Station 6 separated by 10 feet), −23 db (path loss through the human body to the Implanted Wireless Pacemaker 4), +6 dbi (Wireless Monitoring Base Station antenna gain), −10 db (signal margin)=−87 dbm (Wireless Monitoring Base Station receiver sensitivity). It is fairly straightforward to build a highly selective, high compression point receiver with a sensitivity of −87 dbm in the Wireless Monitoring Base Station 6, particularly since low power consumption is not a constraint. Such a receiver would be immune to most interfering RF signals. Also, it is fairly straightforward to build a transmitter power amplifier with an output power of at least +1 dbm in the Implanted Wireless Pacemaker 4 that would stay within the long-term power budget of the Implanted Wireless Pacemaker 4 battery. Also, several of the embodiments in the invention can be used to create a Radiating Element 30 with a gain of at least −20 dbi.

The second embodiment of the invention is comprised of a fractional wavelength ground plane antenna system. The third embodiment of the invention is RF circuitry that has been optimized for the high input impedance of the antenna system. Both embodiments of the invention are connected together and installed in an Implanted Wireless Pacemaker 2, or other implantable medical device.

Figure 3:
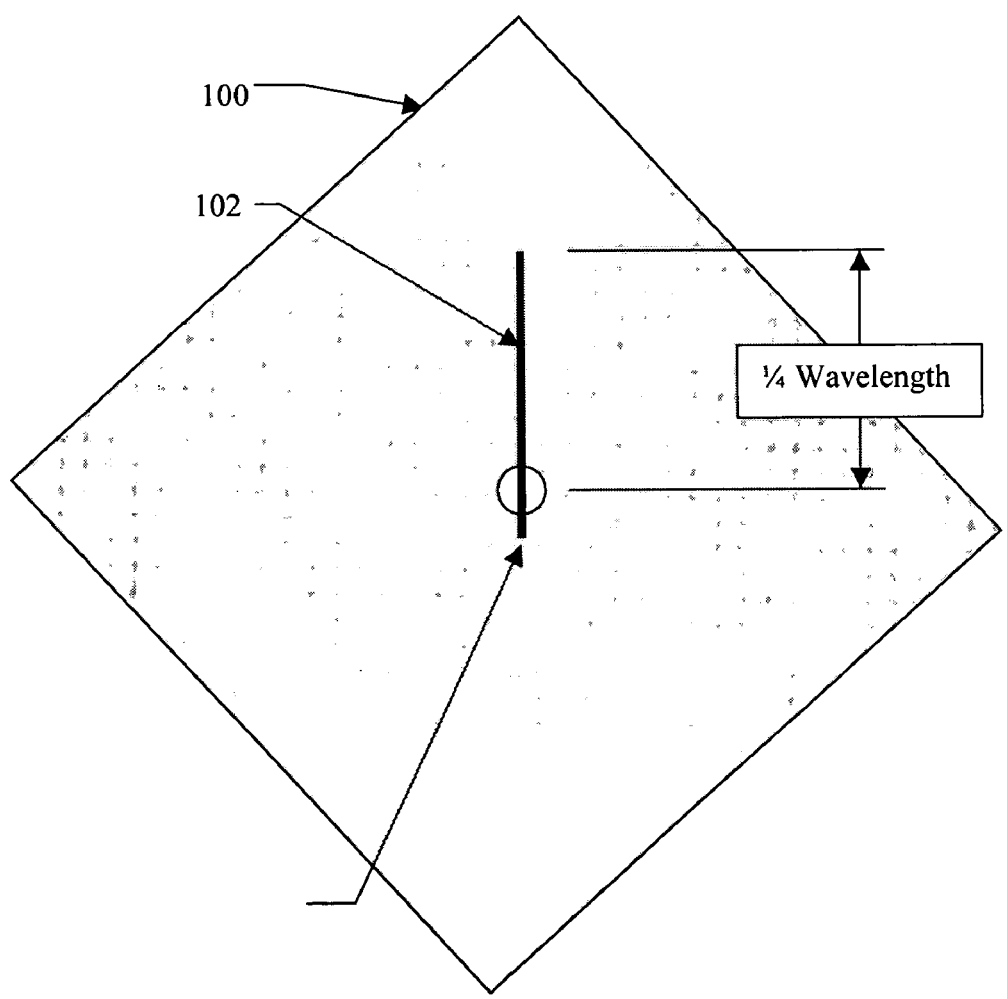
FIG. 3 shows a ¼ wavelength ground plane antenna.

Ground plane antennas are very common in RF communications systems and are traditionally comprised of a conductive radiating element (e.g. a stiff metal rod such as brass) mounted perpendicular to a flat conductive ground plane such that the bottom of the radiating element protrudes through a hole in the middle of the ground plane but is electrically isolated from the ground plane and is supported mechanically by insulating materials. FIG. 3 shows a traditional ground plane antenna with a Metallic Ground Plane 100, and perpendicular Radiating Element 102. The length of the Radiating Element 102 is commonly ¼ of the wavelength of the RF signals of interest. The antenna is electrically connected on the backside of the Metallic Ground Plane 100 by applying a voltage between the end of the Radiating Element 102 (where it protrudes through the Metallic Ground Plane 100) and the Metallic Ground Plane 100 itself. The antenna can be connected directly to transmitter and/or receiver circuitry if the circuitry is located close to the antenna, or a transmission line can be used to connect the antenna to the circuitry. When a Radiating Element 102 of ¼ of the wavelength is used, the input impedance of the antenna is on the order of 50 ohms. If a transmission line is used, for maximum signal transfer between the antenna and the RF circuitry, the characteristic impedance of the transmission line must match the input impedance of the antenna (50 ohms for a ¼ wavelength antenna), and the RF circuitry must be designed to interface to a 50 ohm system. ¼ wavelength ground plane antennas are very efficient radiators of RF energy (they are also very efficient at receiving RF signals).

The major drawback of traditional ground plane antennas is that the physical length of a ¼ wavelength is prohibitively long for many applications. For an RF system operating at 403 MHz, the radiating element of a ¼ wavelength antenna would be about 7.25 inches in length, which is too long for use in a wireless pacemaker.

Figure 4:
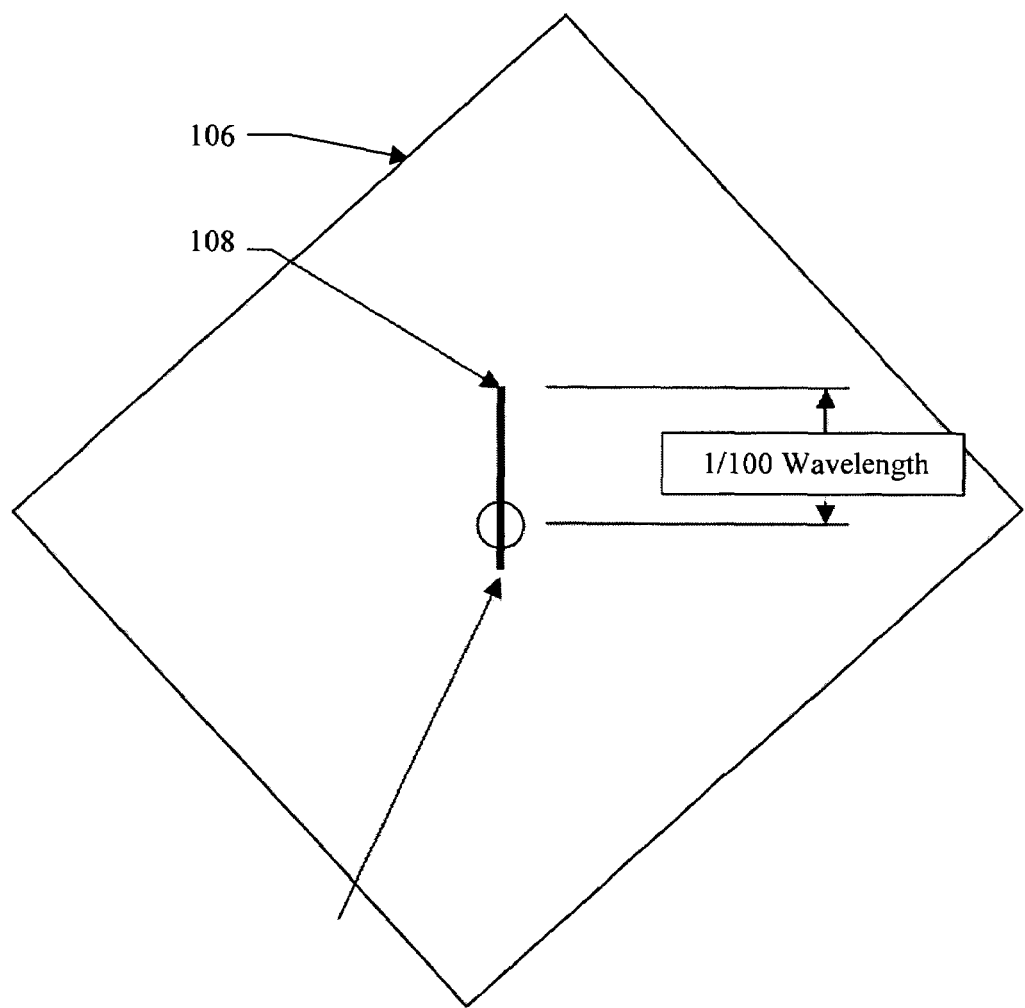
FIG. 4 shows a metallic ground plane and fractional wavelength ground plane antenna.

A fractional wavelength ground plane antenna can be constructed similarly to a traditional ground plane antenna. The main difference is that the Short Radiating Element 108 is much shorter than 1 wavelength. FIG. 4 shows the Metallic Ground Plane of a Fractional Wavelength Ground Plane Antenna 106, the Short Radiating Element 108, which results in a high input impedance. Such an antenna is a much poorer radiator/receiver of RF energy than the traditional ground plane antenna; however, physically it can be much smaller than the traditional antenna. For example, with an RF system operating at 403 MHz, the Short Radiating Element 108 of a 1/100 wavelength antenna would be about 0.29 inches in length, which is practical for many different applications. The present invention uses a variant of the fractional wavelength ground plane antenna in a pacemaker, or other implantable medical device.

The input impedance to a fractional wavelength ground plane antenna is much higher than in a traditional ground plane antenna; therefore, the RF circuitry (including the transmission line, if used) connected to the antenna must be optimized to operate with the higher antenna impedance. If a transmission line must be used, it may be necessary to use a coupling transformer (or other impedance translating device) to match the impedance of the transmission line to the input impedance to the antenna. For the highest power added efficiency, the preferred implementation is to use a power amplifier operating at an output voltage and output impedance that has been optimized to the input impedance of the antenna and is located close enough to the antenna connections to eliminate the need for a transmission line.

In the invention, the fractional wavelength ground plane antenna must be designed such that the Wireless Pacemaker Housing functions as the ground plane, and the radiating element protrudes through the housing so that RF signals can be transmitted and/or received outside of the Wireless Pacemaker Housing. So, instead of the Wireless Pacemaker Housing functioning as a Faraday cage, it is providing the ground plane for the antenna system. The length of the Short Radiating Element 108 will be selected as a trade-off between antenna performance and the transmitter's power consumption (and/or receiver sensitivity) for a given operating distance (range).

In the preferred implementation, the fractional wavelength ground plane antenna is comprised of a Button Antenna that is designed to be attached to the Wireless Pacemaker Housing using the same methods used to attach electrical feed-throughs. When the Button Antenna is constructed of glass, or other appropriate material, it can be installed as part of a hermetic seal. Since the radiating element of the antenna can be short, the height of the button antenna can be kept to a minimum. The target height in a 403 MHz system could be about 0.300 inches, which could be used in a system with an effective operating range of 10 s of feet.

Figure 5:
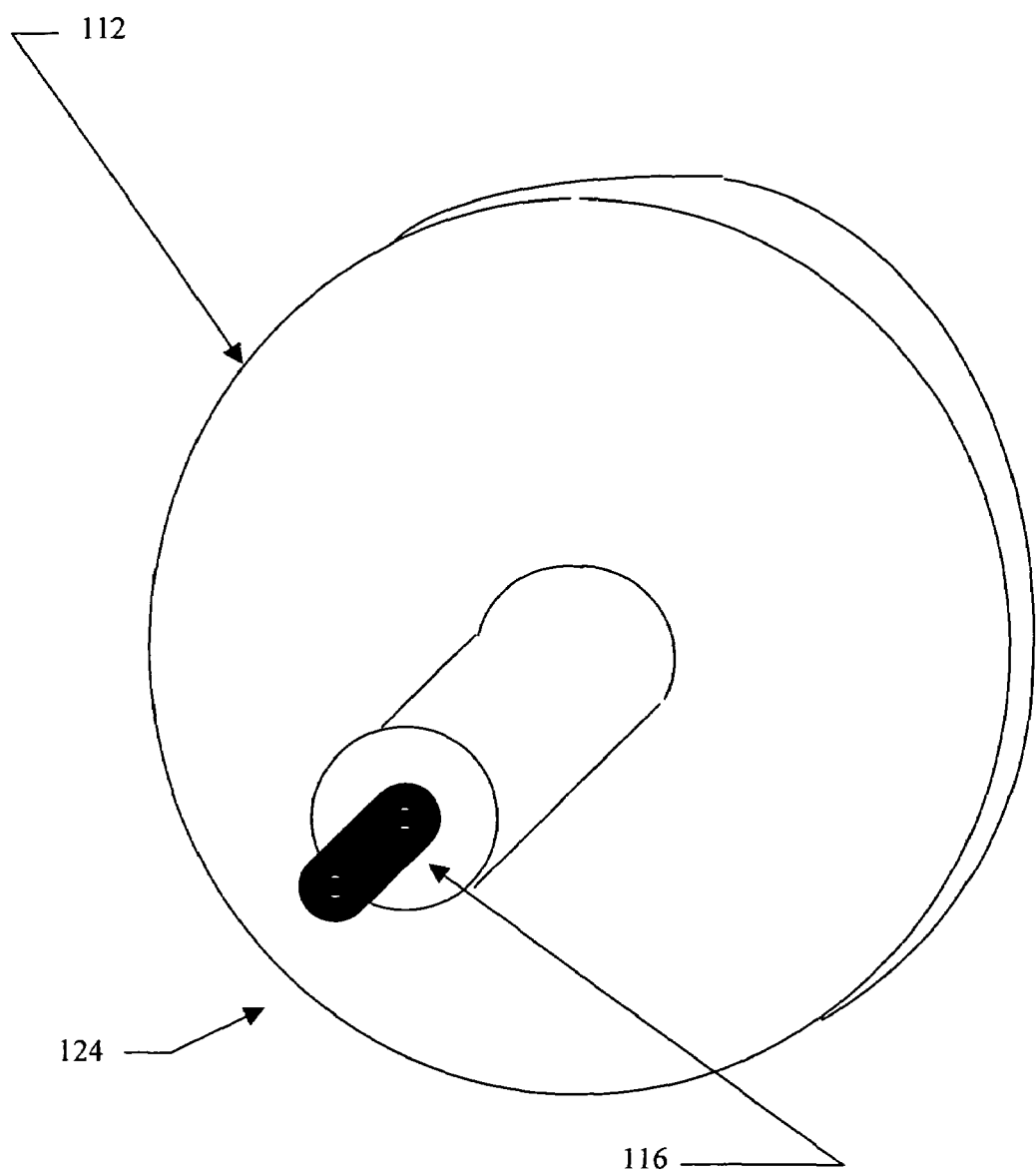
FIG. 5 shows a button antenna for use on the surface of a wireless pacemaker housing.
Figure 6:
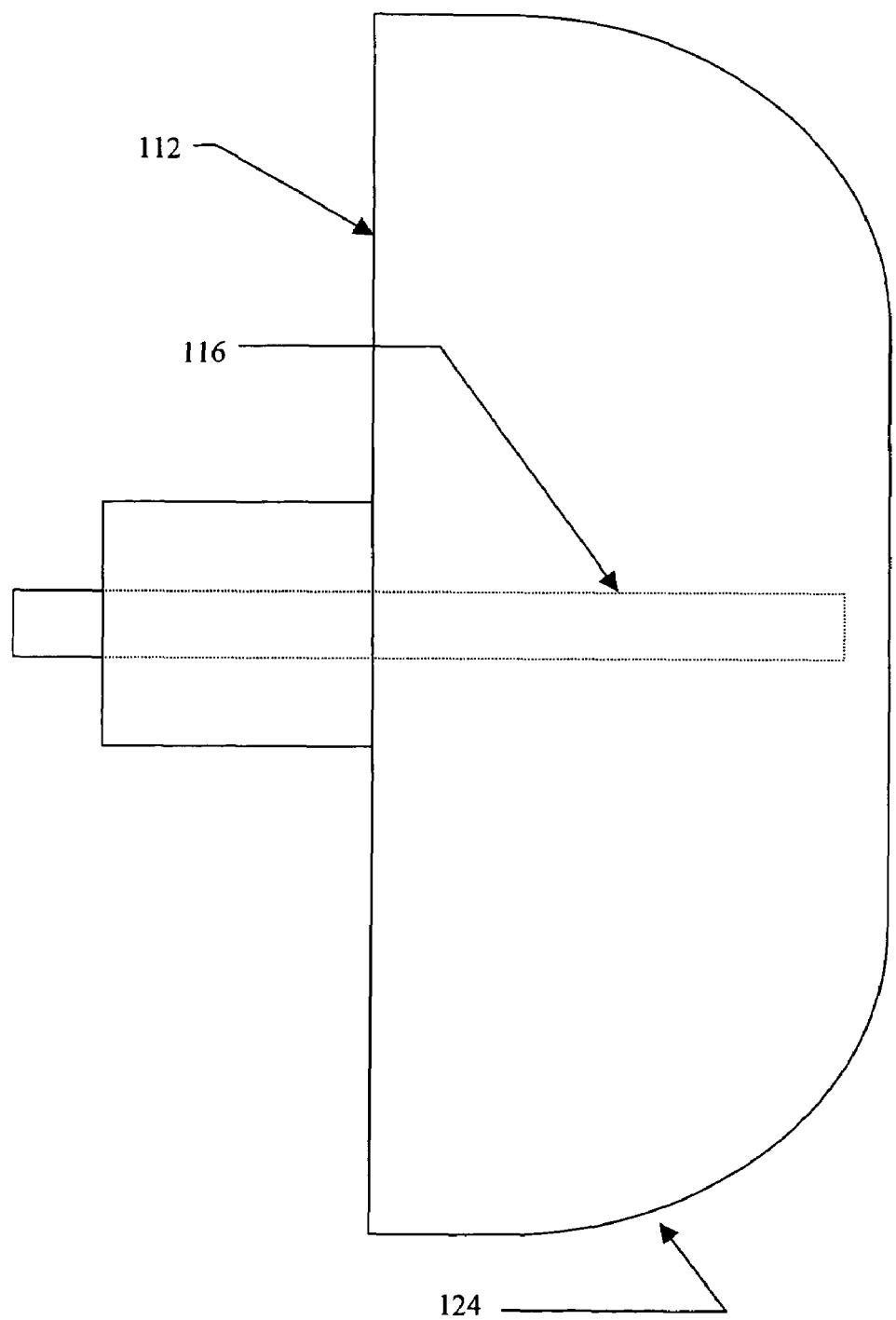
FIG. 6 shows a side view of the button antenna of FIG. 5.

In FIGS. 5 and 6, the Button Antenna 124 is comprised of an Encapsulated Antenna 116 that is completely encapsulated by an Insulating Material Compatible with an Implanted Environment (Preferable Materials are Able to be Hermetically Sealed; examples include Glass or Ceramic) 112. The Encapsulated Antenna 116 must be constructed of a conductive material, such as a brass rod. The portion of the Encapsulated Antenna 116 that extends above the surface of the Wireless Pacemaker Housing is the effective radiating element 108 of the antenna system. The end of the Encapsulated Antenna 116 (or an electrical connection attached to the end of the Encapsulated Antenna 116) protrudes from the insulating material for connection to the RF circuitry inside the Wireless Pacemaker Housing 128. This allows for an electrical connection to the button antenna's encapsulated antenna 116.

Figure 7:
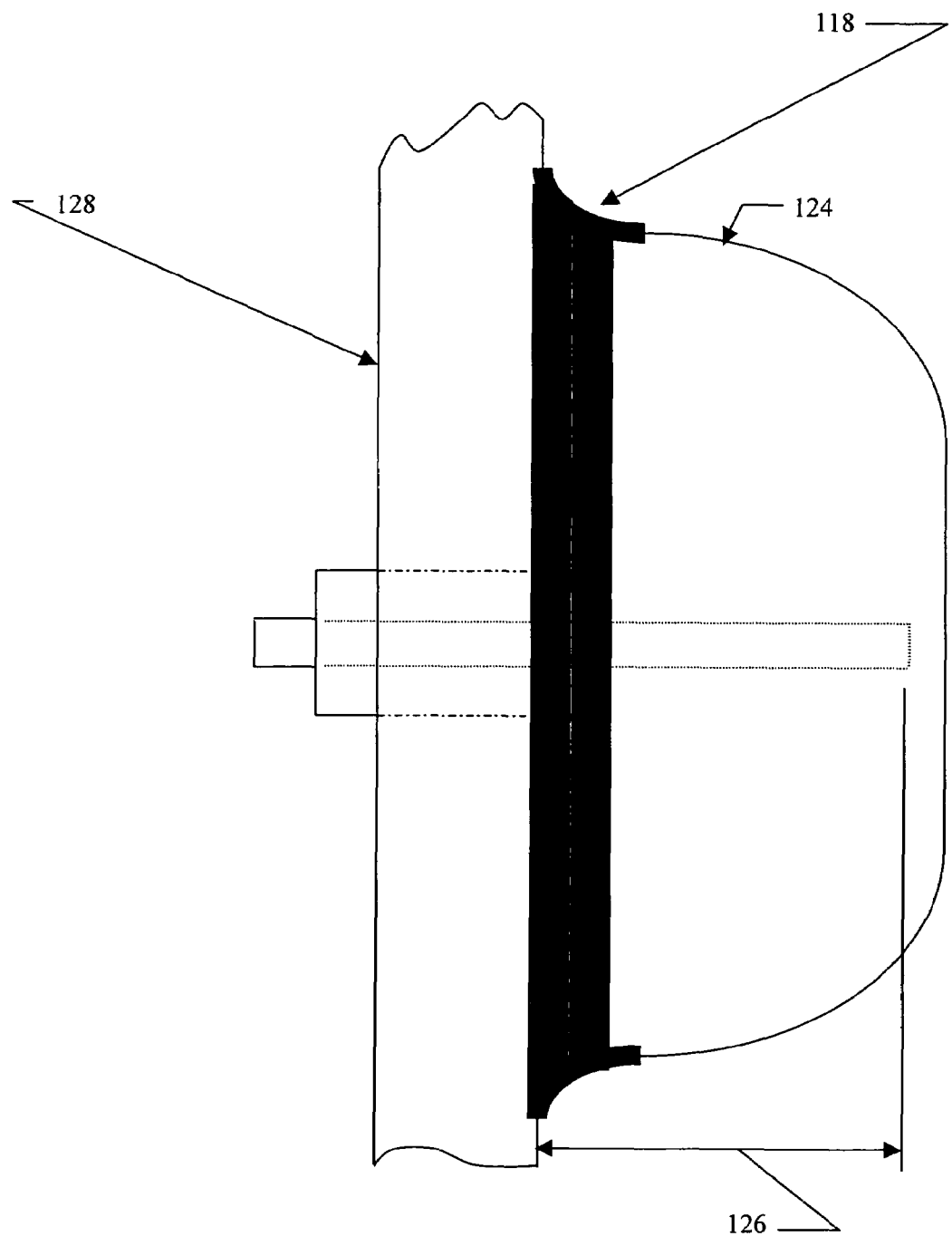
FIG. 7 shows a close up view of the button antenna attached to the surface of the wireless pacemaker housing.
Figure 8:
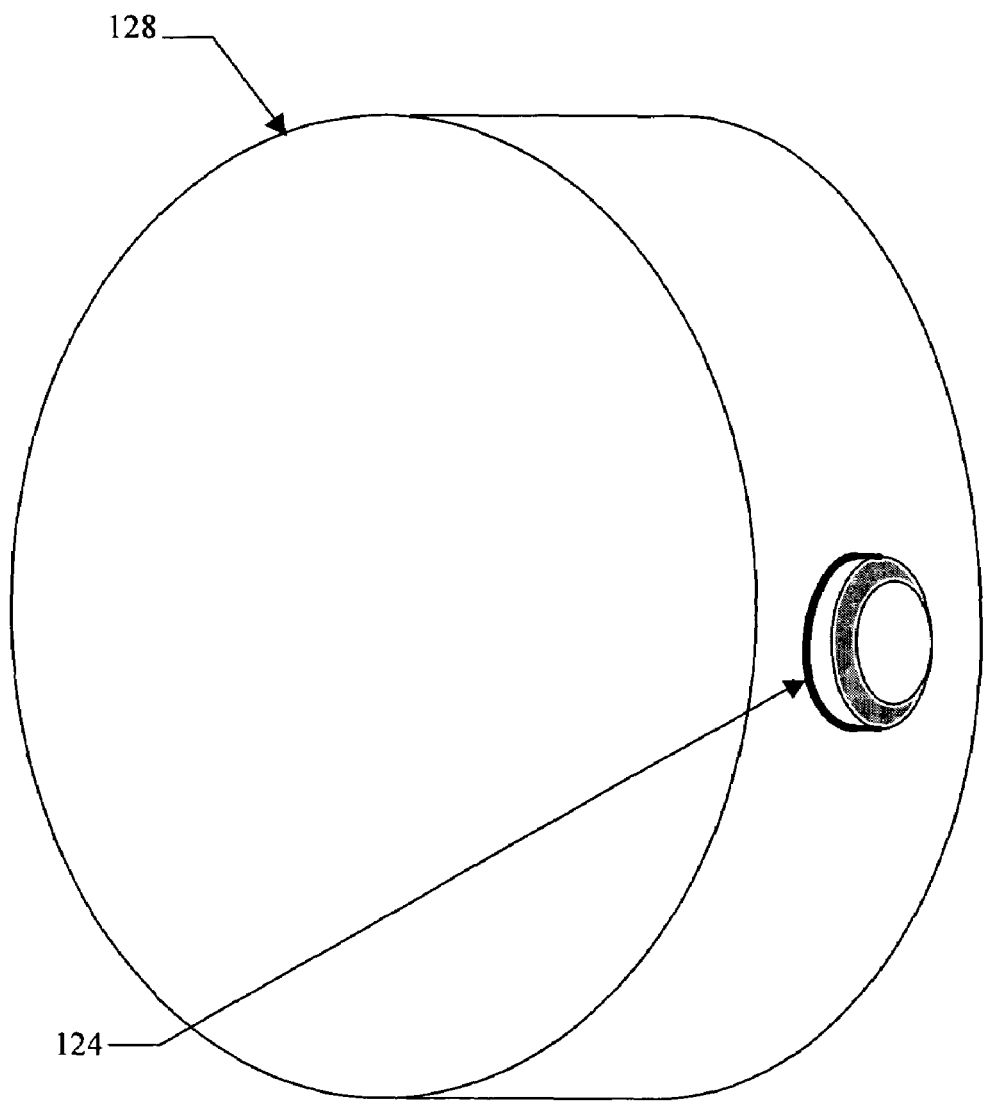
FIGS. 8 and 9 show wide angle views of the wireless pacemaker housing of FIG. 7 with alternative locations of the button antenna on the surface of the housing.
Figure 9:
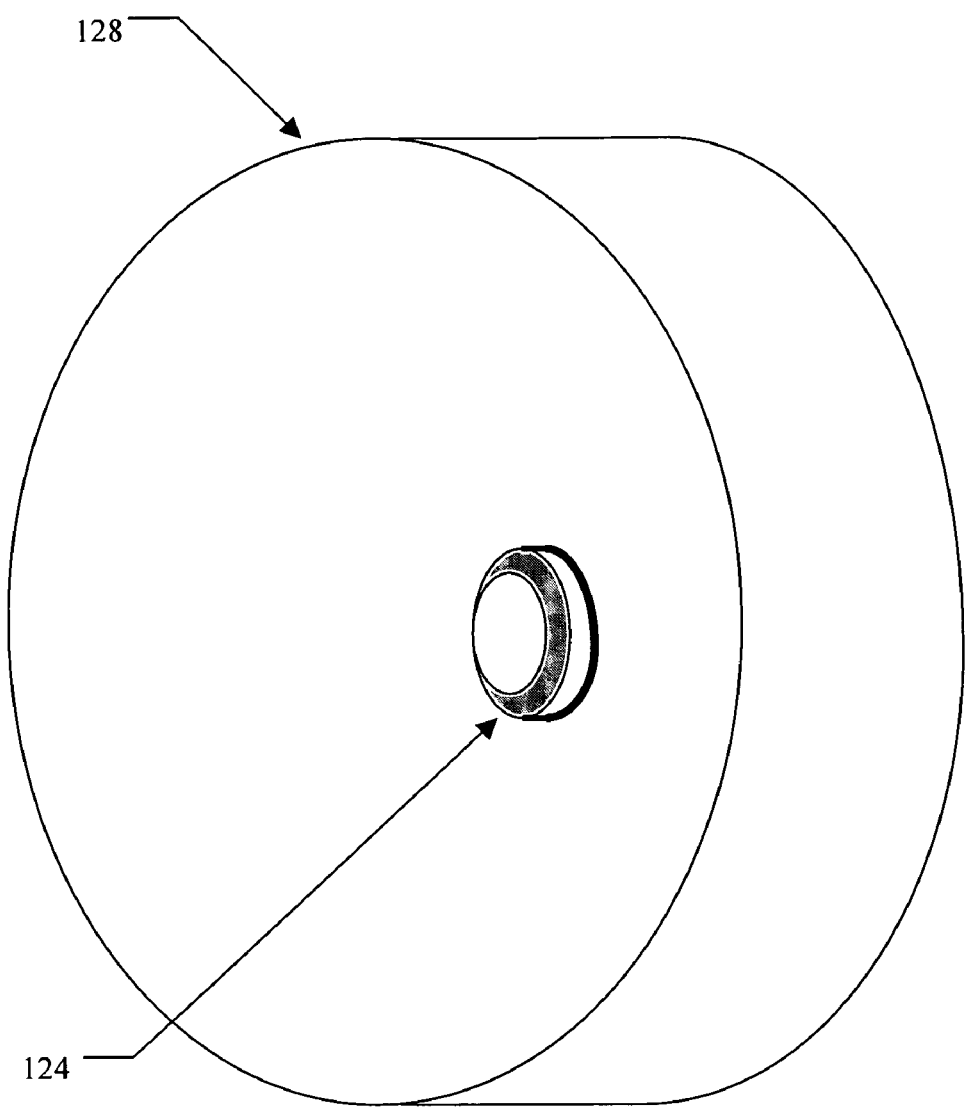

The Button Antenna 124 can be shaped such that it has a low profile when attached to the Wireless Pacemaker Housing 128. FIG. 7 shows part of a Wireless Pacemaker Housing 128 and the Hermetic Attachment 118 of a Button Antenna 124 to a Wireless Pacemaker Housing 128. The Wireless Pacemaker Housing 128 is the ground plane for the Button Antenna 124. The Button Antenna 124 can be of low profile construction since the Electrical and Physical Height 126 of the Button Antenna 124 is a small fraction of the RF Wavelength. The Button Antenna 124 can be attached to the edge of the Wireless Pacemaker Housing 128 (See FIG. 8) or to the front or back of the Wireless Pacemaker Housing 128 (See FIG. 9). The Button Antenna 124 can be designed to preserve the overall shape of the Wireless Pacemaker Housing 128 with only a slight protrusion.

By using the Button Antenna 124 with the appropriate RF circuitry, an effective high frequency RF system can be designed within the practical constraints of current pacemaker technology. The antenna system can be designed to be small enough and be hermetically sealed to be implantable. The RF circuitry can be designed to operate within the voltage and current budget allowed by battery powered systems, while providing enough radiated RF energy to function over an operating range in the tens of feet. The antenna is designed to radiate its power externally to the Wireless Pacemaker Housing 128, so RF radiation from circuitry inside the housing is minimized. High frequency operation allows for use of high data rates. Using existing manufacturing techniques to attach the Button Antenna 124 reduces risk and keeps manufacturing costs low.

Figure 10A:
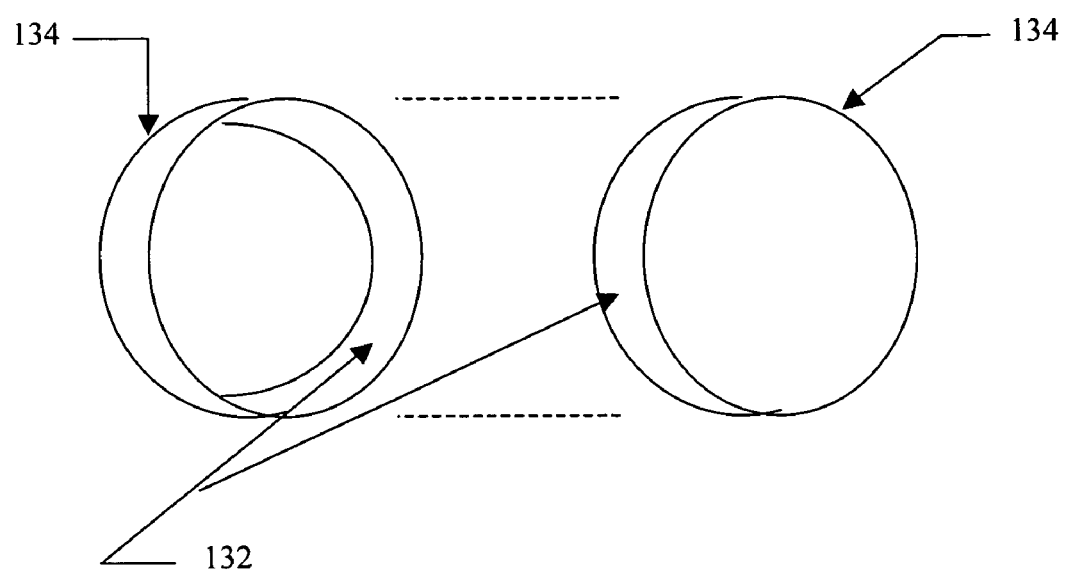
FIG. 10a shows housing halves of a pacemaker.

The fourth embodiment of the invention is to use the Wireless Pacemaker Housing 128 as the transmitting and/or receiving antenna. The completed Wireless Pacemaker Housing 128 is generally shaped in the form of a thick pancake. It is constructed of two halves such that one Pacemaker Housing Half 134 is designed to fit into the other Pacemaker Housing Half 134, similarly to a can of shoe polish with its lid (see FIG. 10A). When the housing is assembled, the halves are electrically insulated from each other using an insulating material 132. The electrical Insulating Material 132 is applied to both Pacemaker Housing Halves 134 to electrically isolate each Housing Half 134 from the other. The Insulating Material 132 could be comprised of a thin non-conducting film coated on each side with non-conducting adhesive to bond the film to each housing half. Alternatively, the insulating material 132 could consist of a non-conducting adhesive containing non-conducting particles (such as large plastic granules) that are large enough to prevent the housing halves from making contact. After assembly, the Wireless Pacemaker Housing 128 is completely sealed with only a thin ring of adhesive and insulator 132 exposed to the environment outside of the Wireless Pacemaker Housing 128. Any leakage path from the outside of the Wireless Pacemaker Housing 128 to the inside of the Wireless Pacemaker Housing 128 through the adhesive and/or insulator 132 would have to traverse from the outside (where only a thin ring of adhesive is exposed) through the Wireless Pacemaker Housing 128 thickness (which is relatively thick) to the inside. This allows for construction of a robust Wireless Pacemaker Housing 128.

Figure 10B:
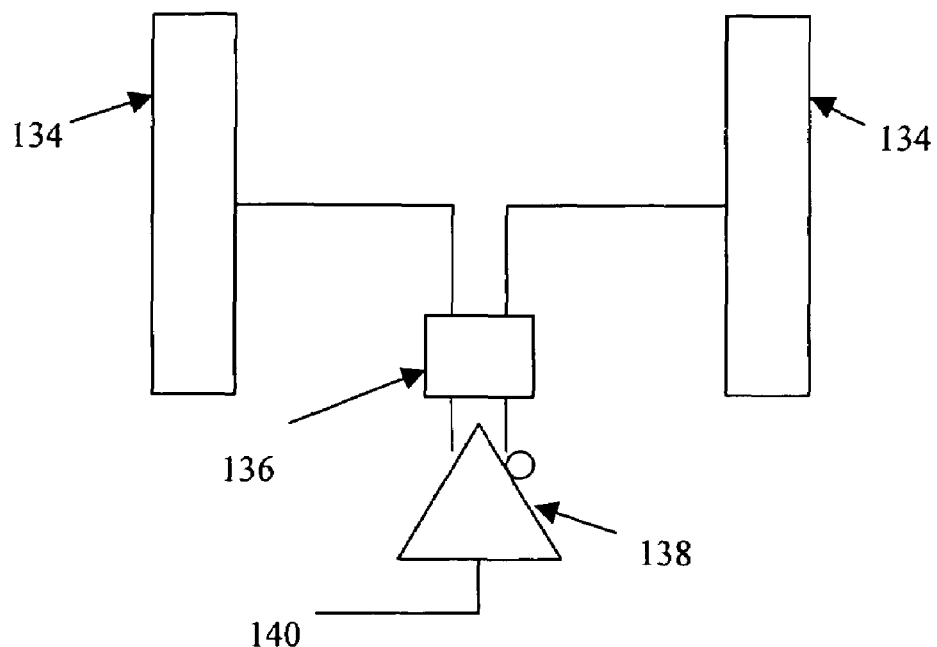
FIG. 10b shows the electrical connection of impedance matching circuits to the housing halves of a pacemaker.
Figure 10C:
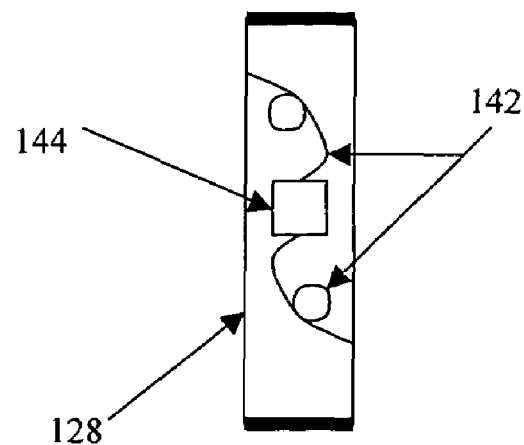
FIG. 10c shows the assembled pacemaker with enclosed impedance matching circuits.

Each Pacemaker Housing Half 134 is electrically driven (from circuitry inside the completed housing) with an RF Transmit Signal 40 feeding a Transmitting RF Power Amplifier 138 (optimized for driving the pacemaker housing when used as a dipole antenna) feeding an Impedance Matching (IM) Network 136 (optimized to provide a matched impedance between the RF Power Amplifier 138 and the transmission line to the Pacemaker Housing Halves 134), which is electrically connected to each Pacemaker Housing Half 134 (See FIG. 10B) on the inside of the completed Wireless Pacemaker Housing 128. In the case of a receiving antenna, the Impedance Matching Network would be connected to an RF Receiver instead of a Transmitting RF Power Amplifier. FIG. 10C shows an assembled wireless pacemaker housing 128 with Electrical Connections 142 to the Pacemaker Housing Halves 134 and the Combined RF Power Amplifier and Impedance Matching Network 144. Conceptually, each Pacemaker Housing Half 134 forms the leg of a dipole antenna. Since the shape of the Wireless Pacemaker Housing 128 may be small (compared to the wavelength of the transmitted signal) or irregularly shaped, and since there is capacitance between the housing halves 134, the Impedance Matching Network 136 is required to maximize the transfer of power from the Power Amplifier to the antenna system (i.e. the housing halves 134).

RF energy is radiated outside of the housing 128 due to the voltage difference between the housing halves 134. The strength of the electric field outside the housing 128 is of the same order of magnitude to that of the electric field inside the housing 128; therefore, the circuitry inside the housing 128 will not be exposed to excessive RF radiation.

Figure 11A:
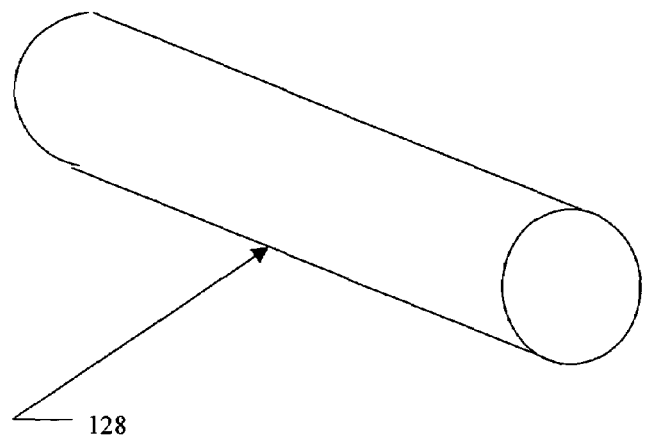
FIG. 11a shows an alternate embodiment of the pacemaker housing in the form of a sealed metal cylinder.

The fifth embodiment of the invention is to use the Wireless Pacemaker Housing 128 as the transmitting and/or receiving antenna. Conceptually, the completed Wireless Pacemaker Housing 128 is such that the Pacemaker Housing 128 is shaped as a cylindrical metal housing with metal ends which have been completely sealed (the Housing 128 is typically constructed of titanium) as shown in FIG. 11A. The Wireless Pacemaker Housing 128 can be completely hermetically sealed (i.e. all exposed surfaces are composed of metal, glass, or ceramic and all joints are sealed by fusion, which is localized melting of the two materials comprising the joint). Generally speaking, hermetically sealed housings provide optimum protection in an implanted environment.

Figure 11B:
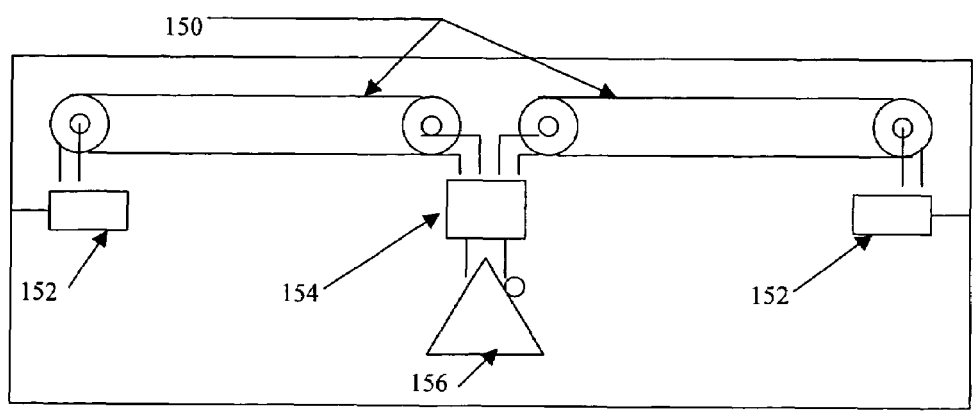
FIG. 11b shows coaxial cables attached to impedance matching circuits within the pacemaker housing.

Each end of the Wireless Pacemaker Housing 128 is electrically driven (from circuitry inside the housing) from a Transmitting RF Power Amplifier 156 (optimized for driving the Coaxial Cables 150 connected to the metal ends of the Wireless Pacemaker Housing 128) feeding an Impedance Matching (IM) Network 154 (optimized to provide a matched impedance between the RF Power Amplifier 156 and the Coaxial Cables 150 connected to the metal ends of the Wireless Pacemaker Housing 128), which is electrically connected to two Coaxial Cables 150 (one for each housing end), each of which is connected to an Impedance Matching Network 152 (optimized to provide a matched impedance between the Coaxial Cables 150 and the metal ends of the Wireless Pacemaker Housing 128), each of which is electrically connected to an end of the Wireless Pacemaker Housing 128 (See FIG. 11B), In the case of a receiving antenna, the Impedance Matching Network 154 would be connected to an RF Receiver instead of a Transmitting RF Power Amplifier. Current will flow between the housing ends, which will radiate RF energy.

If the connection from the RF Power Amplifier 156 and Impedance Matching Network 154 to the housing ends were made using single wires instead of coaxial cables 150, then the magnetic fields from the currents flowing in the single wires would tend to cancel the magnetic fields from the currents flowing in the cylindrical housing 128 which would limit (if not eliminate) the radiated RF energy. Coaxial cables 150 are designed to transfer RF energy from one end of the cable to the other with minimal RF radiation outside the cable (neither electric fields nor magnetic fields appear outside of the cable); therefore, in transferring energy from the RF Power Amplifier 156 and Impedance Matching Network 154 to the housing ends, no canceling magnetic fields are present. It is possible to use other types of transmission lines in place of coaxial cables 150. The goal is to use transmission lines that do not radiate (or radiate minimally).

This concept of driving the housing 128 is not limited to any particular housing size or shape. The housing's effectiveness as a radiator of RF energy will depend upon housing size or shape, but a variety of shapes and sizes can be used, depending upon the application and the radiation efficiency desired (at the operating wavelength). The Impedance Matching Networks 154 and the coaxial cable lengths must be optimized to maximize the transfer of power from the Power Amplifier 156 to the antenna system (i.e. the housing).

RF energy is radiated outside of the housing 128 due to the net magnetic field resulting from the current flow through the housing 128. The length of the housing along which the current flows has inductance, and since this inductance radiates RF energy it can be thought of as a radiating inductor. Since the conducted RF signals inside the housing 128 are transferred using coaxial cable 150, the only electric fields inside the housing 128 exist as a gradient due to the voltage between the housing ends. Since this voltage is relatively small (since the housing is metal), the circuitry inside the housing 128 will not be exposed to excessive RF radiation.

Figure 12:
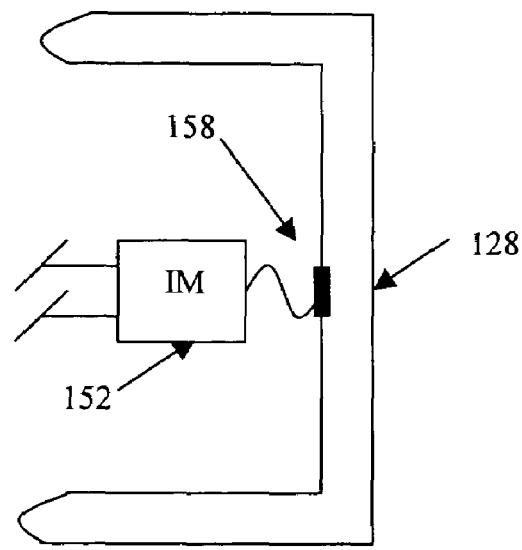
FIG. 12 shows the connection of an impedance matching network to a pacemaker housing.

For ease of construction and to create a Wireless Pacemaker Housing 128 of the highest integrity, it is desirable to make an Electrical Connection 158 between the Wireless Pacemaker Housing 128 and the Impedance Matching Network 152 to the inside of the housing ends (See FIG. 12); however, due to the propensity of RF currents to flow down the inside surface of the housing 128 from one end to the other, it may be possible to create a more efficient antenna by making the electrical connections to the outside of the Wireless Pacemaker Housing 128 (instead of the inside) so that the RF currents tend to flow on the outside surface of the Wireless Pacemaker Housing 128. The intention is to still provide a Wireless Pacemaker Housing 128 of the highest integrity (i.e. hermetically sealed).

Figure 13:
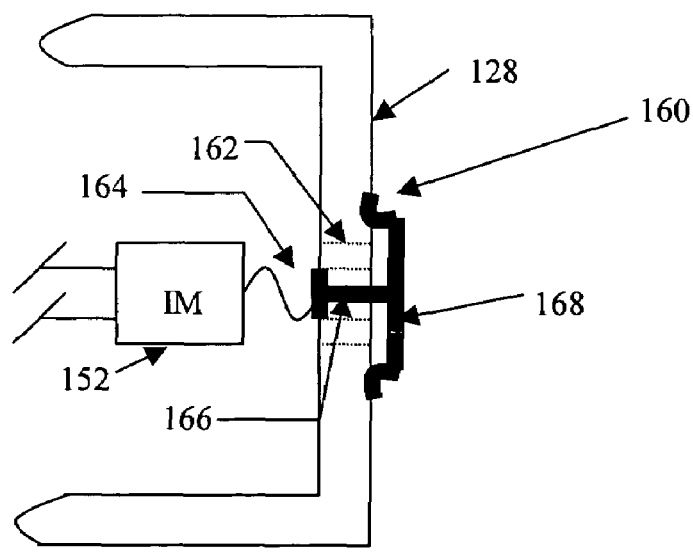
FIGS. 13-16 show the connection of an impedance matching network to the pacemaker using different kinds of electrical feed-thrus.

One approach is to install electrical feed-thrus in each end of the housing (See FIG. 13). An electrical feed-thru is a small donut shaped device with a conducting metallic core surrounded by the Insulating Part 162 (Typical Materials are Glass or Ceramic). The bond between the metallic core and the glass is typically hermetic. The electrical feed-thru is installed in a hole in the housing end (preferably such that the bond is hermetic). There is an Electrical Connection 164 Between the conducting part of the feed-thru facing the inside of the Pacemaker Housing 128 and the Impedance Matching Network 152 (attached to the end of the coaxial cable 150), which is typically soldered. The outside surface of the Wireless Pacemaker Housing 128 is electrically attached to the metallic core of the feed-thru on the outside of the Wireless Pacemaker Housing 128. This could be achieved using a Conductive Metal Disk 168 (typical material is gold), which has an Electrical Connection 166 between the conducting part of the feed-thru facing the outside of the Pacemaker Housing 128 and the Metal Disk. There is an Electrical Connection and Hermetic Seal 160 between the metal disk and the Pacemaker Housing 128 (a technique like Heli Brazing can provide such a connection/seal).

Figure 17:
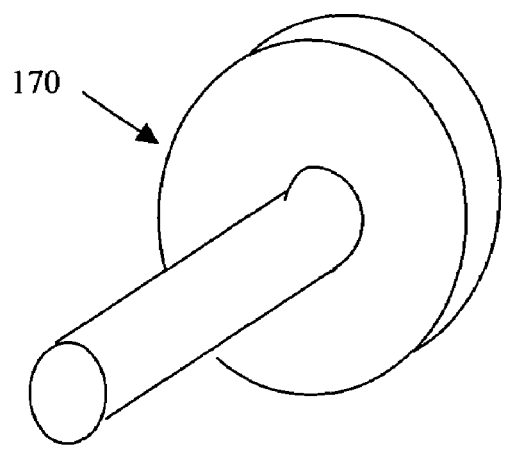
FIG. 17 shows a conductive metal disk with a protruding post similar to the post and disk of FIG. 14.

Another method for making an electrical connection from circuitry inside the Wireless Pacemaker Housing 128 to outside the Wireless Pacemaker Housing 128 is to use a Conductive Metal Disk with a Protruding Post 170 (typical material is gold or gold alloy) (See FIG. 17). The Wireless Pacemaker Housing 128 has a clearance hole at the location of attachment. The Conductive Metal Disk with a Protruding Post 170 is attached to the Wireless Pacemaker Housing 128 such that there is an Electrical Connection and Hermetic Seal 160 Between the Metal Disk and the Pacemaker Housing 128 such that the post faces toward the inside of the housing 128 (See FIG. 14). The post does not touch the Pacemaker Housing 128 or make any electrical contact with the clearance hole. There is an Electrical Connection 172 between the end of the Post on the Metal Disk 170 and the Impedance Matching Network 152.

Another method for making an electrical connection from circuitry inside the housing 128 to outside the housing 128 is to again use a Conductive Metal Disk with a Protruding Post 170. The housing 128 has a hole at the location of attachment. The Conductive Metal Disk with a Protruding Post 170 is attached to the Wireless Pacemaker Housing 128 such that there is an Electrical Connection and Hermetic Seal 160 between the metal disk and the Pacemaker Housing 128 such that the post faces toward the inside of the housing 128 (See FIG. 15). In this method, the Post on the Metal Disk 170 is either swaged or sealed to the inside of the Pacemaker Housing 128. Again, there is an Electrical Connection 160 between the end of the Post on the Metal Disk 170 and the Impedance Matching Network 152. This method works if the electrical conductivity of the metal used in the Wireless Pacemaker Housing 128 is much lower than the electrical conductivity of the metal used in the post (e.g. the conductivity of gold is about 10 times greater than the conductivity of certain titanium alloys).

Figure 16:
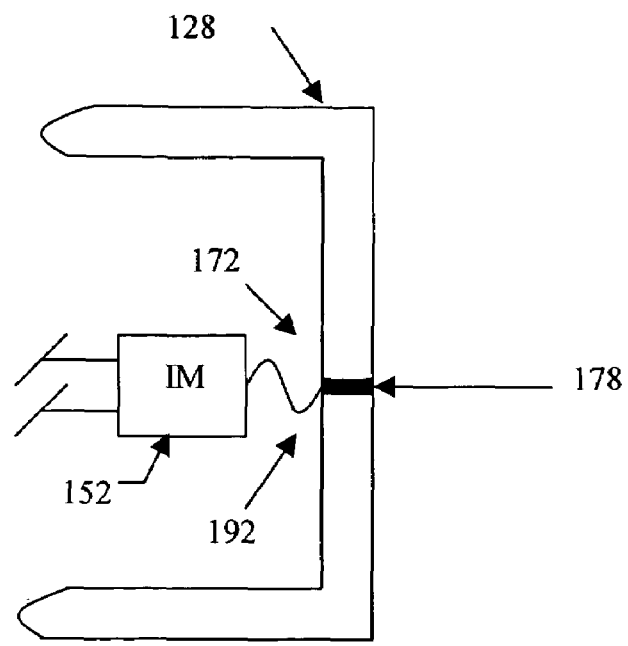
Figure 18:
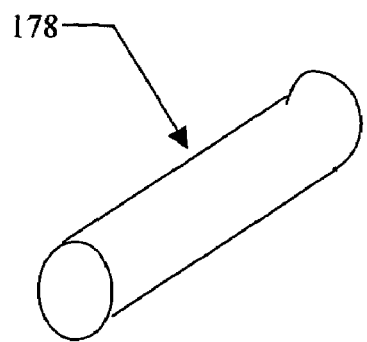
FIG. 18 shows a conductive metal post without the disk of the type used in FIG. 14.

A variation on the above method for making an electrical connection from circuitry inside the Wireless Pacemaker Housing 128 to outside the Wireless Pacemaker Housing 128 is to use a Conductive Metal Post 178 (typical material is gold or gold alloy) (See FIG. 18). Again, the housing 128 has a hole at the location of attachment. The Conductive Metal Post 178 is swaged and/or hermetically sealed to the inside and outside of the Pacemaker Housing 128 (See FIG. 16). The swaging and/or sealing of the metal post provides an electrical attachment of the metal post 178 to the outside surface of the Wireless Pacemaker Housing 128. This method works if the electrical conductivity of the metal used in the Wireless Pacemaker Housing 128 is much lower than the electrical conductivity of the metal used in the post 178 (e.g. the conductivity of gold is about 10 times greater than the conductivity of certain titanium alloys).

Figure 21:
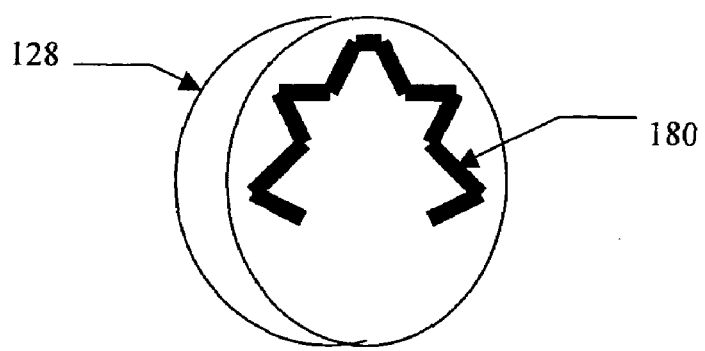
FIG. 21 shows an embodiment of the antenna created by selectively plating highly conductive metals onto the pacemaker housing in one of multiple patterns.
Figure 26:
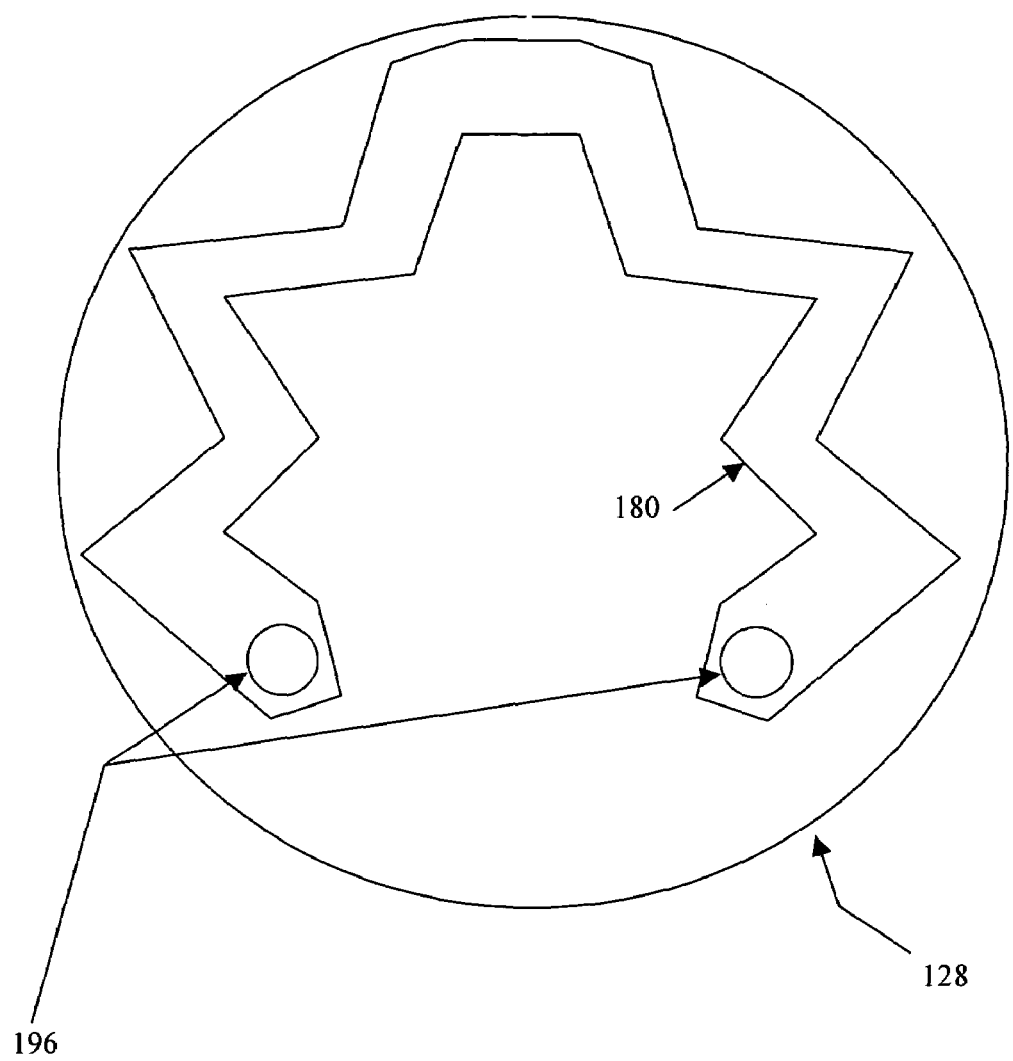
FIG. 26 shows an antenna and metal disks with posts within the wireless pacemaker housing.

The sixth embodiment of the invention is to create an antenna by selectively plating highly conductive metals (such as silver or gold) onto the outside surface of the Wireless Pacemaker Housing 128, and then making electrical connections from the circuitry inside the housing to the plated antenna using the techniques described above. Antenna designs can be created for housings of multiple shapes and sizes. To illustrate the concept, consider a housing shaped in the form of a thick pancake (See FIG. 21). By Selective Plating 180, a highly conductive metal, such as gold, can be bonded to the surface of the Wireless Pacemaker Housing 128 to form a modified loop antenna. Other styles of antennas can be used (e.g. patch antennas). As before, the housing can be completely hermetically sealed. FIG. 26 shows Selective Plating 180 as an antenna and Metal Disks with Posts 196 connecting the inside of the Wireless Pacemaker Housing 128 to the Plated Antenna 180 on the outside surface of the Wireless Pacemaker Housing 128.

Typically, the plated antenna 180 would be electrically driven from inside the Wireless Pacemaker Housing 128 from a Transmitting RF Power Amplifier feeding an Impedance Matching Network which is electrically connected to two coaxial cables (one for each antenna feed point), each of which is connected to an Impedance Matching Network, each of which is electrically connected to the feed points of the plated antenna 180 via inside to outside connections (in the case of a receiving antenna, the Impedance Matching Network would be connected to an RF Receiver instead of a Transmitting RF Power Amplifier). The feed points of the plated antenna 180 may be relatively close together which may allow the use of single wires or other transmission lines in place of the coaxial cables.

Figure 19:
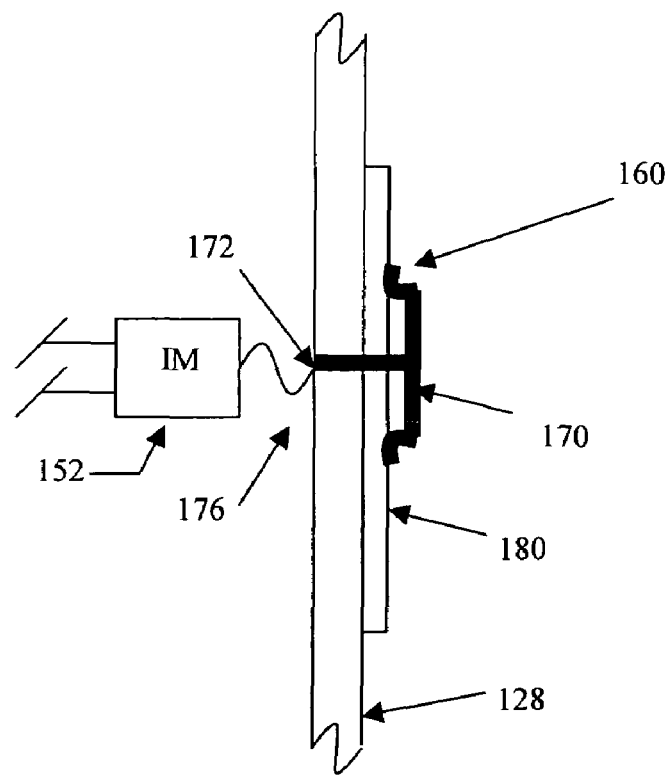
FIG. 19 shows an embodiment of the feed-thru of FIGS. 14 and 15, but further including selective plating on the surface of the pacemaker housing.

A method for making the electrical connection from circuitry inside the housing to the Selective Plating 180 antenna on the surface of the housing 128 is to again use a Conductive Metal Disk with a Protruding Post 170. The housing has a hole at the location of attachment. The Conductive Metal Disk with a Protruding Post 170 is attached to the Wireless Pacemaker Housing 128 such that there is an Electrical Connection and Hermetic Seal 160 between the metal disk and the Pacemaker Housing 128 where the antenna has been selectively plated 180. The post is oriented to face toward the inside of the housing 128 (See FIG. 19). In this method, the Post on the Metal Disk 170 is either swaged or sealed to the inside of the Pacemaker Housing 128. Again, there is an Electrical Connection 160 between the end of the Post on the Metal Disk 170 and the Impedance Matching Network 152. This method works if the electrical conductivity of the metal used in the Wireless Pacemaker Housing 128 is much lower than the electrical conductivity of the metal used in the post (e.g. the conductivity of gold is about 10 times greater than the conductivity of certain titanium alloys).

Figure 20:
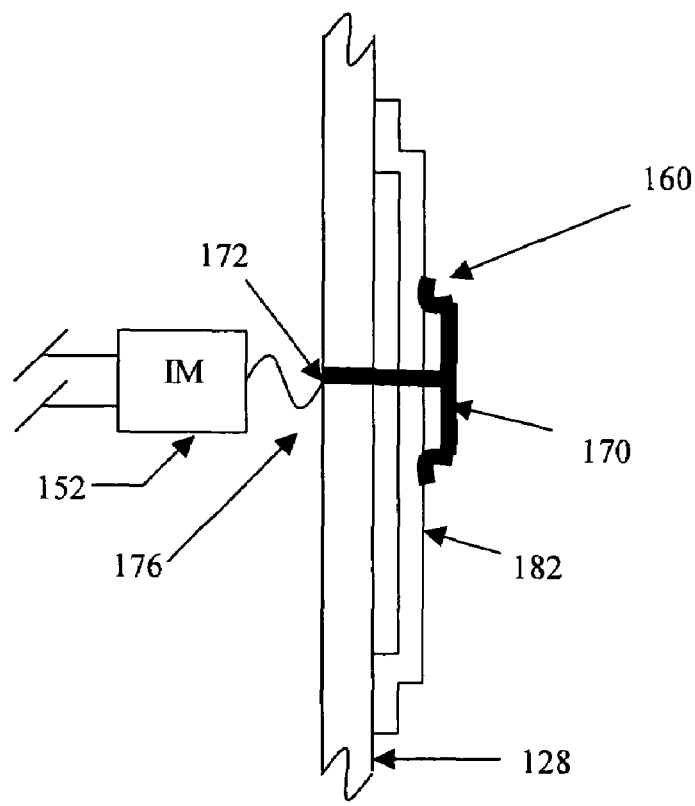
FIG. 20 shows an embodiment of the feed-thru largely the same as that of FIG. 19, but using a double plating on the surface of the pacemaker housing.
Figure 22:
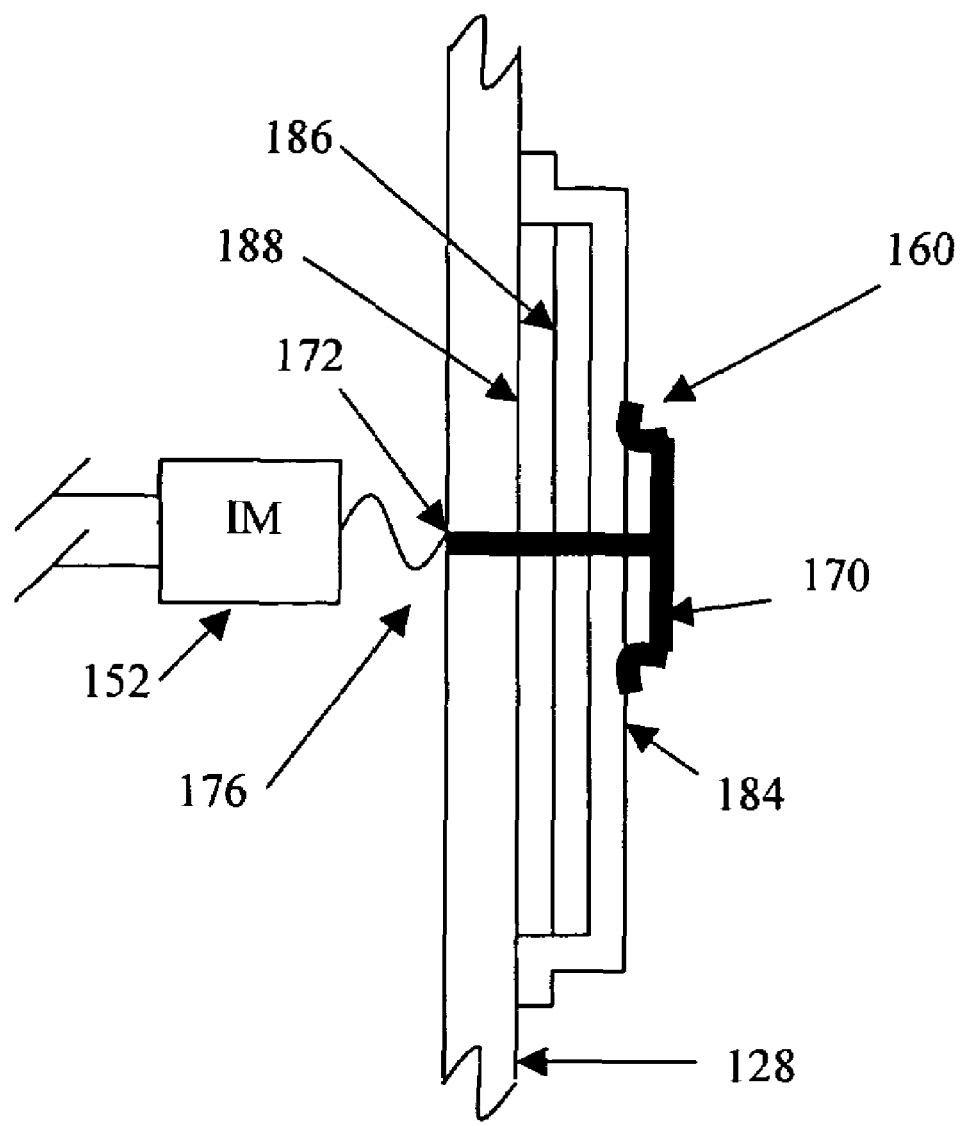
FIG. 22 shows an embodiment of the antenna including a metalized insulating material.

This method is also effective if Selective Double Plating 182 is used, wherein a very high conductivity metal is selectively plated onto the Wireless Pacemaker Housing 128, such as silver, and a protective metal is plated over it which is compatible with implantation, such as gold (see FIG. 20). A third variant is to use an Insulating Material 184 under the Selective Plating 180. This material is attached to the housing 128, and a protective metal is plated over it which is compatible with implantation (again, such as gold). A metalized insulating material 184 (comprised of a non-conducting Dielectric 188 with a Metallization Coating 186 plated on one side) could be used (See FIG. 22), again with a protective metal plated over it (the Metallization 186 could provide the primary conduction path, with the protective metal layer on top).

Figure 14:
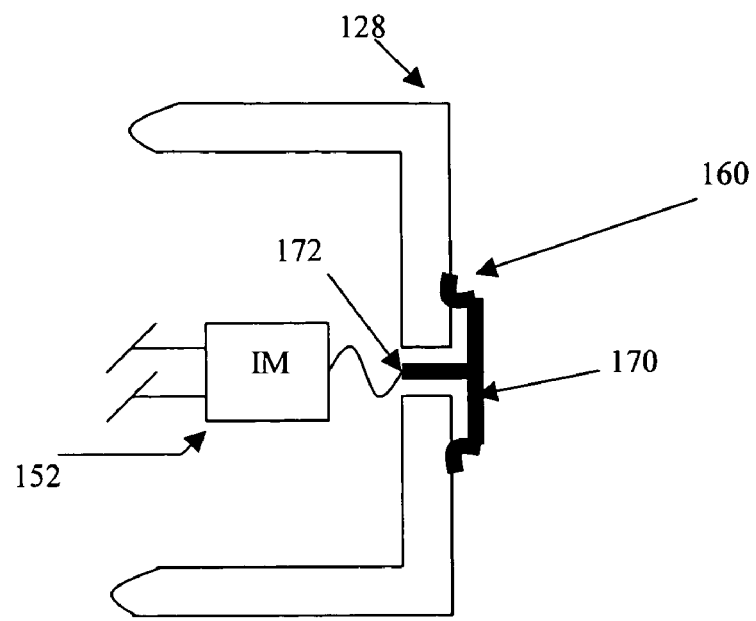
Figure 15:
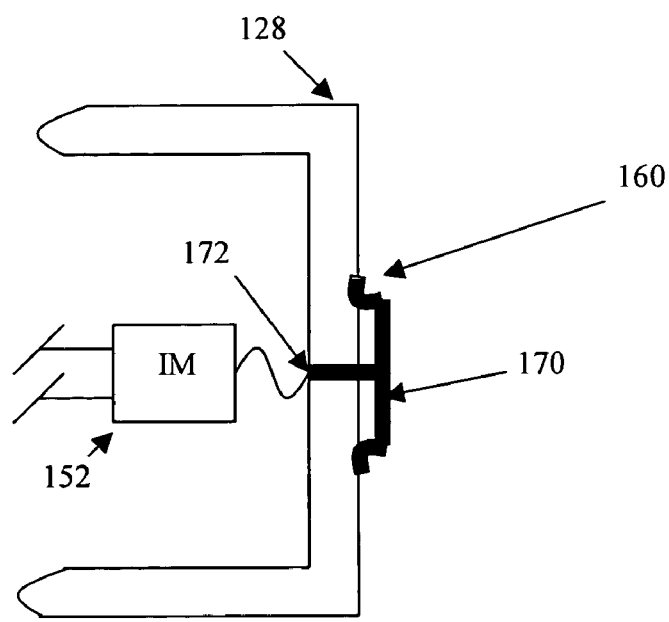

Any of the methods from FIG. 13, FIG. 14, or FIG. 15 could be adapted as the means for connecting the circuitry to the plated antenna 180. Also, a Conductive Metal Post 178 could be used in place of the Conductive Metal Disk with a Protruding Post 170 (As shown earlier in FIG. 16 and FIG. 18). The Conductive Metal Post 178 is swaged and/or hermetically sealed to the inside and outside of the Pacemaker Housing 128 before the final selective plating layer is applied. The electrical connection is made between the Metal Post 178 and the Plating 180 during the plating process as shown in FIG. 23.

Figure 23:
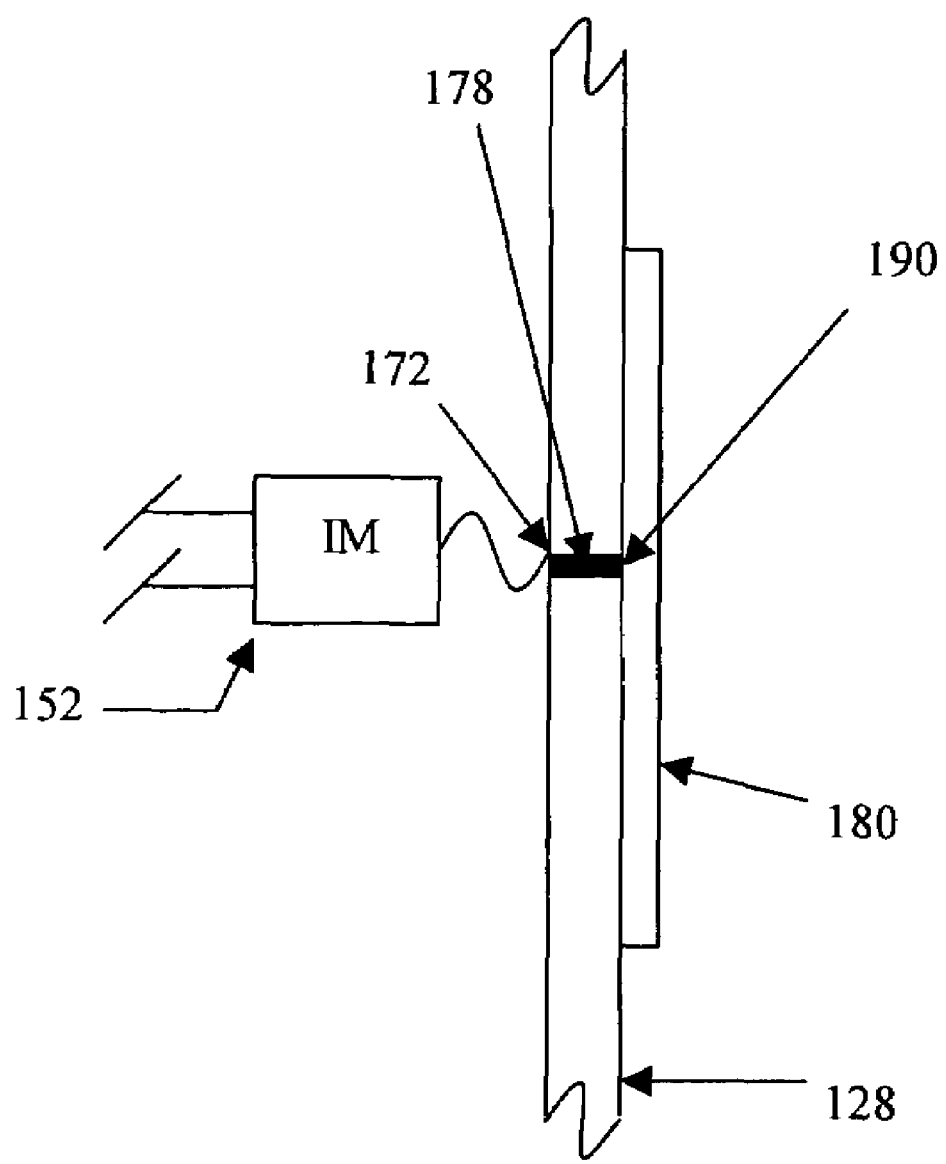
FIGS. 23-25 show other embodiments of the feed-thru with a swaged metal post and selective metalized plating layers.
Figure 24:
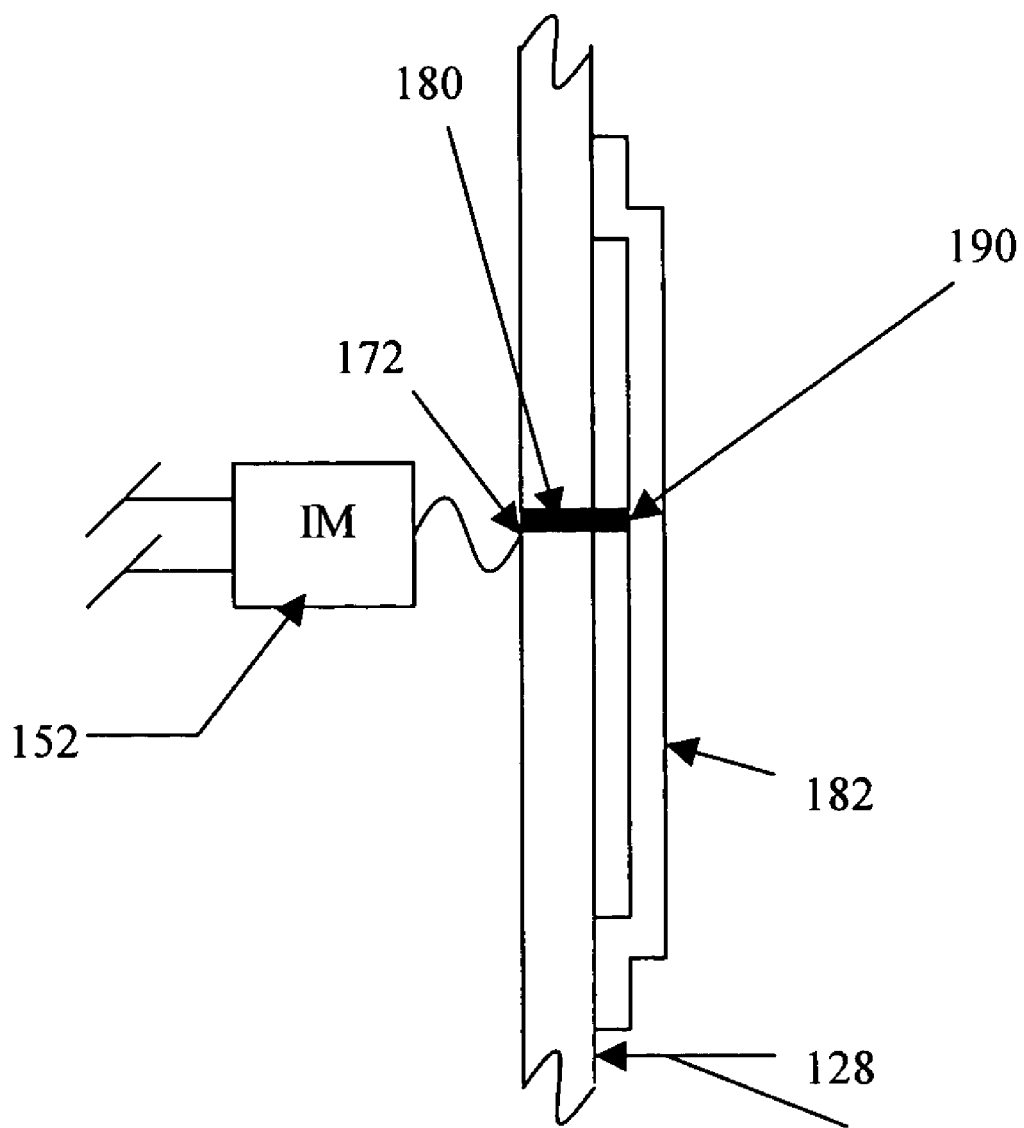
Figure 25:
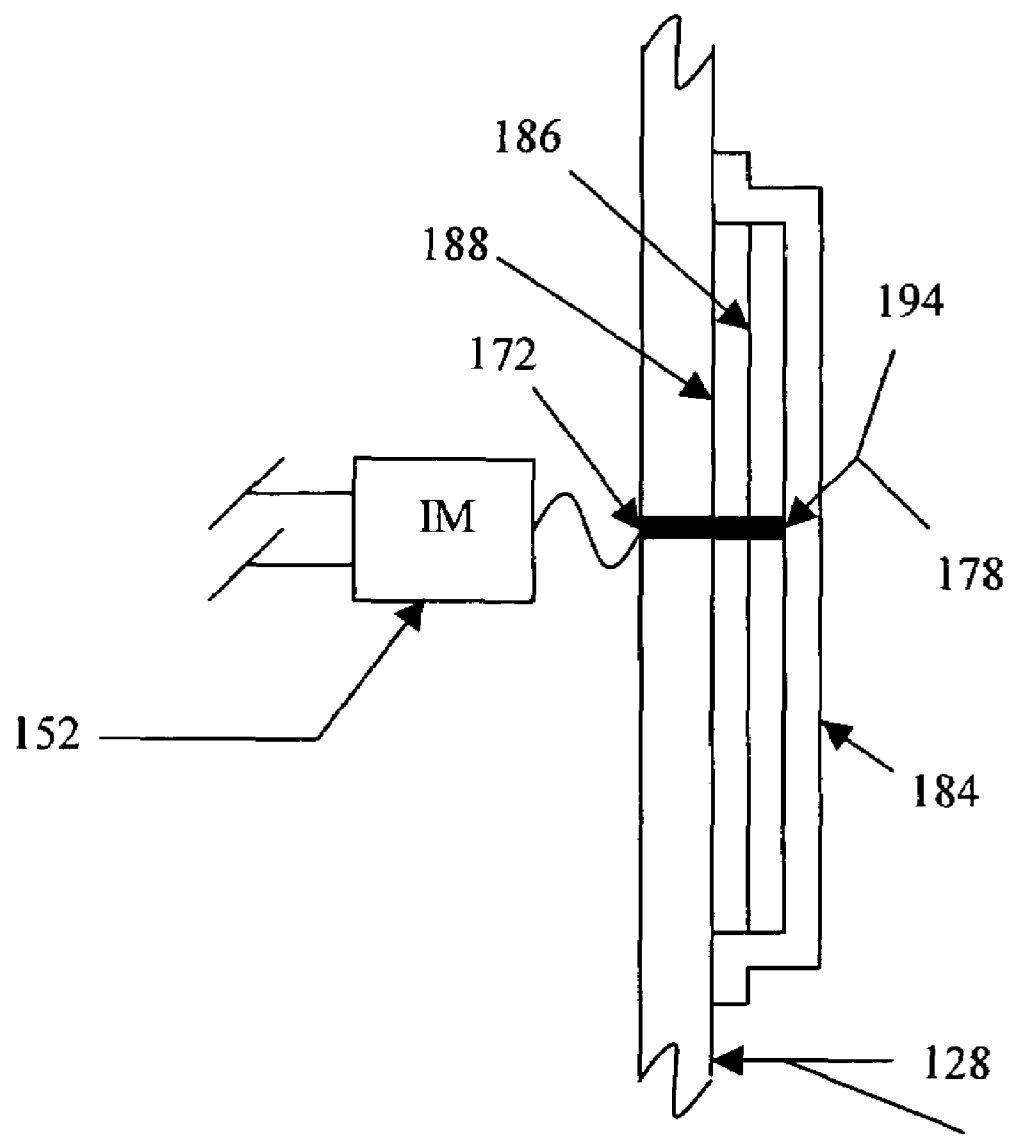

When the final selective plating layer is applied directly to the Wireless Pacemaker Housing 128, the Conductive Metal Post 178 is swaged and/or hermetically sealed to the inside and outside of the Pacemaker Housing 128 (See FIG. 23). When the final selective plating layer is applied over a base plating layer (i.e. selective double plating), the Conductive Metal Post 178 is swaged and/or hermetically sealed to the inside of the Pacemaker Housing 128 and the outside of the base plating layer (See FIG. 24). When the final selective plating layer is applied over a plated or metalized insulator, the Conductive Metal Post 178 is swaged and/or hermetically sealed to the inside of the Pacemaker Housing 128 and the metallization side of the Metalized Insulator 194 (See FIG. 25). After the Conductive Metal Post 178 has been installed, when the final selective plating layer is applied, the Conductive Metal Post 178 will be electrically connected to the final plating layer. Also, depending on the process, the plating will provide a hermetic seal at the post 178.

When using a plated antenna 180 on the Wireless Pacemaker Housing 128, since the housing is made of metal, its conductivity works to short out the antenna elements; therefore, this method is only effective if the electrical conductivity of the metal used in the Wireless Pacemaker Housing 128 is much lower than the electrical conductivity of the metal used in the plated antenna (e.g. the conductivity of gold is about 10 times greater than the conductivity of certain titanium alloys, the conductivity of silver is more than 20 times greater than the conductivity of certain titanium alloys) and the pathways that would short out the antenna elements are long enough to allow the antenna to be effective. In general, thick, narrow plating would provide antenna patterns of relatively low resistance and low shorting pathways. Also, plating thicknesses greater than the housing thickness increase the resistance of the shorting pathways. Also, if a plating over insulator process is used, the only electrical connection from the plating to the housing is at the edges of the selective plating 180 (since the insulator is between the housing and the plating). This essentially increases the resistance of the shorting pathways.

Traditional printed antenna designs can be implemented using this process. The effectiveness of any specific antenna design will be degraded due to the conductivity of the housing. A strong benefit of this approach is the effectiveness of the housing 128 in shielding the circuitry inside the housing 128 from the RF energy being radiated from the antenna.

Figure 27:
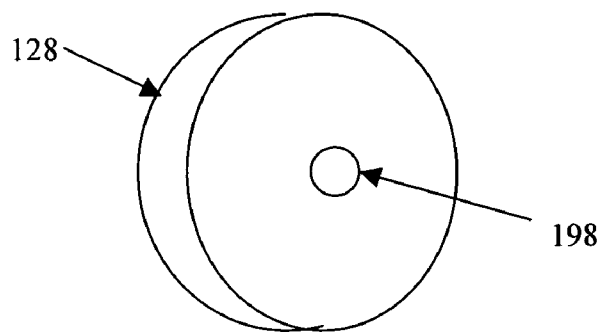
FIGS. 27 and 28 show apertures within a completed pacemaker housing.
Figure 28:
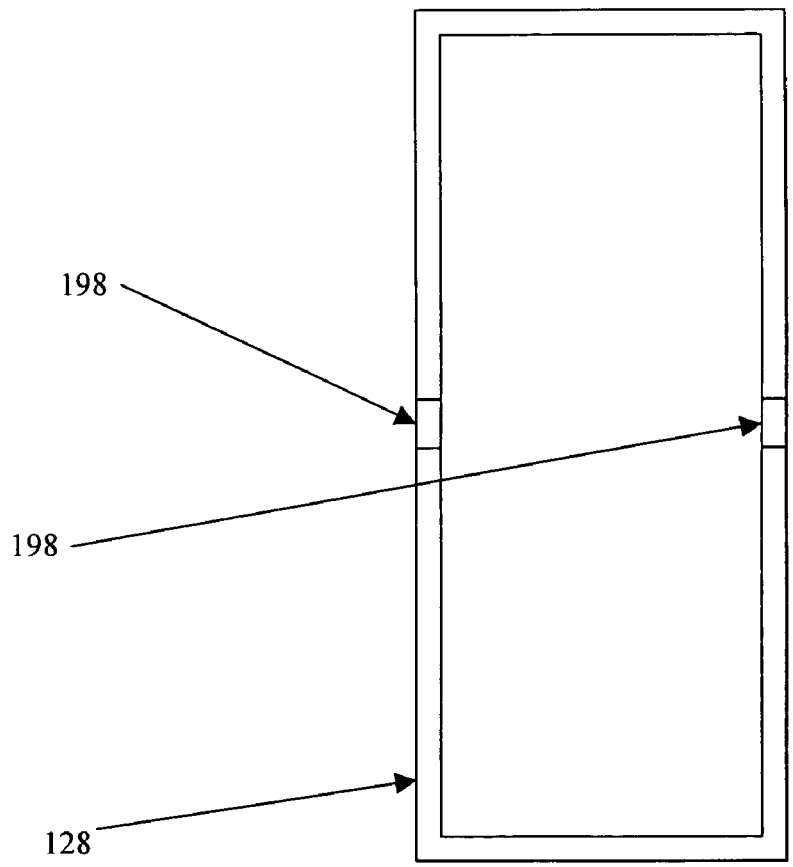

The seventh embodiment of the invention is to create an antenna system using strategically placed apertures in the housing to allow RF energy to radiate from inside the housing 128 to outside the housing 128 (in the case of a receiving antenna, the RF energy would penetrate the apertures and be received by the antenna). Conceptually, the Pacemaker Housing 128 is shaped as a cylindrical metal housing with metal ends which have been completely sealed (the Housing 128 is typically constructed of titanium) such that the completed Wireless Pacemaker Housing 128 is generally shaped in the form of a thick pancake. It has two Apertures 198 which are essentially holes in the metal Wireless Pacemaker Housing 128 (in the center on each side of the pancake, see FIG. 27 and FIG. 28). Each Aperture 198 plugs the hole with either glass or ceramic which is sealed to the Wireless Pacemaker Housing 128 (it is preferred that the seals be hermetic); therefore, the housing 128 can be completely hermetically sealed.

Figure 29:
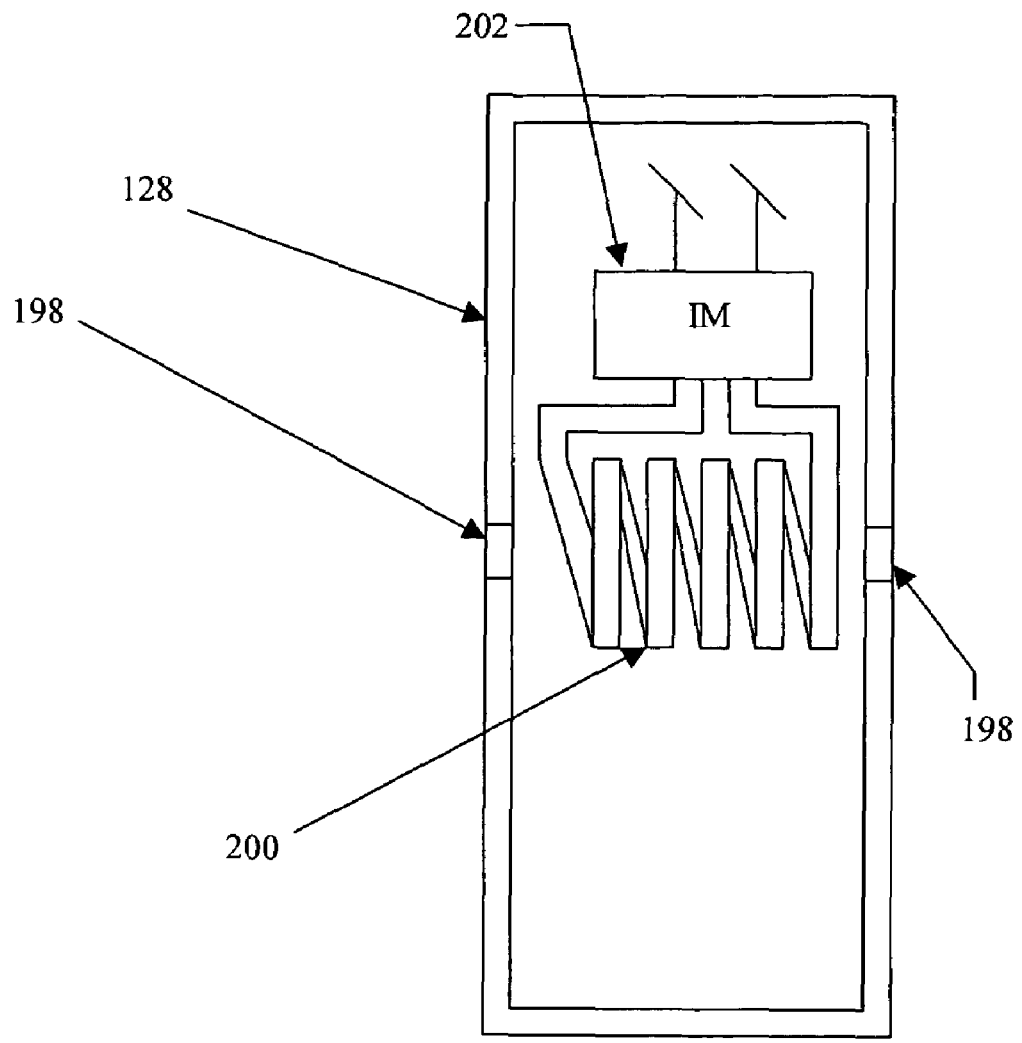
FIGS. 29 and 30 show impedance matching circuits and radiating coils relative to apertures inside a pacemaker housing.
Figure 30:
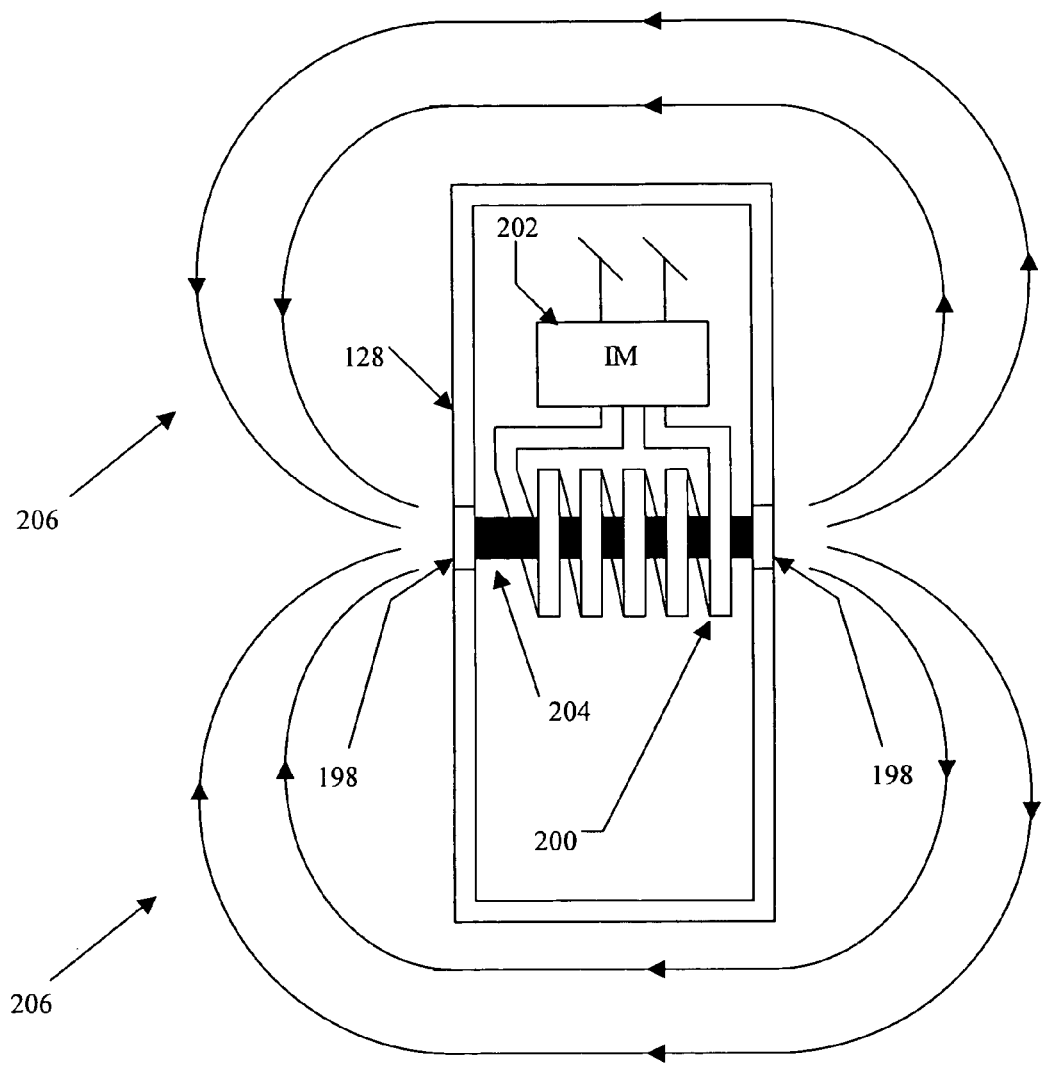

A Transmitting RF Power Amplifier feeds an Impedance Matching Network 202 (optimized to provide a matched impedance between the RF Circuitry and the Radiating Coil 200), which is electrically connected to a Radiating Coil 200 (also known as a Radiating Inductor). The coil 200 is oriented such that its magnetic field is aligned with the two apertures 198 (See FIG. 29). Some of the magnetic field escapes from the housing 128 and radiates as RF energy. If the coil is equipped with a Magnetic Core 204, such as ferrite, which is closely aligned with the apertures 198, more of the magnetic field can be directed outside of the housing 128. FIG. 30 illustrates the Lines of Magnetic Radiation 206.

RF energy is radiated outside of the Wireless Pacemaker Housing 128 due to the net magnetic field escaping from the housing resulting from the current flow through the Radiating Coil 200 (since the Radiating Coil 200 is essentially an inductor that radiates RF energy it can be thought of as a radiating inductor). Since the Wireless Pacemaker Housing 128 is conductive, and since the housing surrounds the Radiating Coil 200, it tends to act as a shorted turn. For example, if the inductor is viewed as the primary winding of a transformer, and the Wireless Pacemaker Housing 128 is viewed as the secondary winding of the transformer which is shorted, the shorted secondary winding will absorb some of the energy from the magnetic field that is shared by the housing and the Radiating Coil 200. The higher the conductivity of the housing 128, the more energy that will be absorbed.

This concept of RF energy escaping through apertures 198 is not limited to any particular Wireless Pacemaker Housing 128 size or shape. The housing's effectiveness in allowing RF energy to escape will depend upon Wireless Pacemaker Housing's size or shape and aperture location, size, or shape; however, a variety of shapes and sizes can be used, depending upon the application and the radiation efficiency desired (at the operating wavelength). The Impedance Matching Network 202 and the Radiating Coil 200 design must be optimized to maximize the transfer of power from the Power Amplifier to the antenna system.

Since a Radiating Coil 200 is used as the radiating element, the voltages involved are not large enough to cause large electric fields. Also, since the net magnetic field will be radiating through the apertures 198, the circuitry inside the Wireless Pacemaker Housing 128 will not be exposed to excessive RF radiation.

Those skilled in the art will recognize improvements and modifications to the preferred embodiments of the present invention. All such improvements and modifications are considered within the scope of the concepts disclosed herein and the claims that follow.

We claim:

1. A pacemaker comprising:
   a) wireless communication electronics;
   b) control circuitry associated with the wireless communication electronics and adapted to:
      i) monitor patient information of a patient;
      ii) provide pacing signals to the patient; and
      iii) communicate with a base station via the wireless communication electronics using spread spectrum communications to receive information for controlling the pacemaker from the base station; and
   c) a housing, which encloses the wireless communication electronics and the control circuitry and forms at least in part an antenna.

2. The pacemaker of claim 1 wherein the antenna is associated with the wireless communication electronics for wireless communications.

3. The pacemaker of claim 1 wherein the control circuitry transmits the patient information to the base station via spread spectrum communications.

4. The pacemaker of claim 1 wherein the control circuitry receives information for controlling the pacing signals from the base station via spread spectrum communications.

5. The pacemaker of claim 1 wherein the antenna comprises at least one radiating element.

6. The pacemaker of claim 5 wherein the housing further comprises a first section and a second section.

7. The pacemaker of claim 5 wherein the antenna further comprises a ground plane.

8. The pacemaker of claim 7 wherein the housing substantially provides the ground plane.

9. The pacemaker of claim 8 wherein the ground plane and the at least one radiating element form a fractional wavelength ground plane antenna.

10. A pacemaker comprising:
    a) wireless communication electronics;
    b) control circuitry associated with the wireless communication electronics and adapted to:
       i) monitor patient information of a patient;
       ii) provide pacing signals to the patient; and
       iii) communicate with a base station via the wireless communication electronics; and
    c) a housing:
       i) comprising a first section and a second section wherein the first section is substantially electrically insulated from the second section; and
       ii) which encloses the wireless communication electronics and the control circuitry and forms at least in part an antenna comprising at least one radiating element.

11. The pacemaker of claim 10 wherein the first section and the second section provide the at least one radiating element.

12. The pacemaker of claim 11 wherein the first section and the second section substantially form a dipole antenna.

13. A pacemaker comprising:
    a) wireless communication electronics comprising a plurality of substantially powered-down states and a plurality of substantially powered-up states; and
    b) control circuitry associated with the wireless communication electronics and adapted to:
       i) monitor patient information of a patient;
       ii) provide pacing signals to the patient; and
       iii) communicate with a base station using slow frequency hopping spread spectrum communications via the wireless communication electronics.

14. The pacemaker of claim 13 wherein the wireless communications electronics sends a first transmission using a radio frequency carrier having a first frequency, and sends a second transmission using a radio frequency carrier having a second frequency.

15. The pacemaker of claim 13 wherein the wireless communications electronics receives a first reception from a radio frequency carrier having a first frequency, and receives a second reception from a radio frequency carrier having a second frequency.

16. The pacemaker of claim 13 wherein an average time duration of the plurality of substantially powered-down states is more than ten times an average time duration of the plurality of substantially powered-up states.

17. The pacemaker of claim 13 wherein the base station transmits an interrogation signal from a radio frequency carrier having a first frequency, and the wireless communications electronics scans a plurality of spread spectrum channels during the transmission of the interrogation signal.

18. The pacemaker of claim 17 wherein the base station waits for a reply following transmission of the interrogation signal.

19. The pacemaker of claim 18 wherein the wireless communications electronics transmits a reply from a radio frequency carrier having the first frequency.

* * * * *